(12) United States Patent
Ng et al.

(10) Patent No.: US 7,938,921 B2
(45) Date of Patent: May 10, 2011

(54) STRAND COMPOSITE HAVING LATENT ELASTICITY

(75) Inventors: Wing-Chak Ng, Suwanee, GA (US); Janis Wilson Hughes, Alpharetta, GA (US); Patricia H. Calhoun, Alpharetta, GA (US); Glynis Allicia Walton, Roswell, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 608 days.

(21) Appl. No.: 11/603,954

(22) Filed: Nov. 22, 2006

(65) Prior Publication Data

US 2008/0119103 A1    May 22, 2008

(51) Int. Cl.
   *B29C 65/66* (2006.01)
(52) U.S. Cl. ............. 156/84; 156/85; 156/178; 156/229
(58) Field of Classification Search ............ 156/84, 156/85, 167, 176, 178, 179, 181, 229
   See application file for complete search history.

(56) References Cited

U.S. PATENT DOCUMENTS

| | | |
|---|---|---|
| 3,086,242 A | 4/1963 | Cook et al. |
| 3,338,992 A | 8/1967 | Kinney |
| 3,341,394 A | 9/1967 | Kinney |
| 3,354,506 A | 11/1967 | Raley |
| 3,494,821 A | 2/1970 | Evans |
| 3,502,538 A | 3/1970 | Petersen |
| 3,502,763 A | 3/1970 | Hartmann |
| 3,542,615 A | 11/1970 | Dobo et al. |
| 3,639,917 A | 2/1972 | Althouse |
| 3,650,649 A | 3/1972 | Schippers |
| 3,692,618 A | 9/1972 | Dorschner et al. |
| 3,801,429 A | 4/1974 | Schrenk et al. |

(Continued)

FOREIGN PATENT DOCUMENTS

EP    1184014 A2    3/2002

(Continued)

OTHER PUBLICATIONS

Search Report and Written Opinion for PCT/IB2007/053952, Feb. 13, 2008.

(Continued)

*Primary Examiner* — Michael A Tolin
(74) *Attorney, Agent, or Firm* — Dority & Manning, P.A.

(57) ABSTRACT

A nonwoven composite that exhibits latent elastic properties is provided. The composite is formed from an elastic strand layer laminated to a nonwoven web facing. Latent elasticity may be imparted to the elastic strand layer through the combination of a thermoplastic elastomer and a polyolefin capable of forming semi-crystalline domains among the elastomeric chains. More specifically, the elastic strand layer may be stretched in one or more directions to orient the elastomer chains. Without intending to be limited by theory, the present inventors believe that the oriented state of the chains may be held in place by the relatively stiff semi-crystalline domains of the polyolefin. The stretched elastic strand layer may subsequently be relaxed and bonded to a nonwoven web facing to form the composite. The composite may be later activated (e.g., heated) to shrink the elastic strand layer and provide it with "latent" stretchability. For instance, the composite may be heated at or above the softening temperature of the polyolefin to soften the crystalline domains and allow the chains to return to their unoriented state. As a result of the present invention, the elastic strand layer may be extended and recover from its unoriented state.

31 Claims, 3 Drawing Sheets

U.S. PATENT DOCUMENTS

| | | | |
|---|---|---|---|
| 3,802,817 A | 4/1974 | Matsuki et al. |
| 3,849,241 A | 11/1974 | Butin et al. |
| 3,912,565 A | 10/1975 | Koch et al. |
| RE28,688 E | 1/1976 | Cook |
| 4,041,203 A | 8/1977 | Brock et al. |
| 4,144,370 A | 3/1979 | Boulton |
| 4,323,534 A | 4/1982 | DesMarais |
| 4,340,563 A | 7/1982 | Appel et al. |
| 4,374,888 A | 2/1983 | Bornslaeger |
| 4,527,990 A * | 7/1985 | Sigl ............... 604/385.29 |
| 4,543,154 A | 9/1985 | Reiter |
| 4,552,795 A | 11/1985 | Hansen et al. |
| 4,640,726 A | 2/1987 | Sallee et al. |
| 4,640,859 A | 2/1987 | Hansen et al. |
| 4,663,106 A | 5/1987 | Pomplun et al. |
| 4,663,220 A | 5/1987 | Wisneski et al. |
| 4,665,306 A | 5/1987 | Roland et al. |
| 4,680,450 A | 7/1987 | Thorson et al. |
| 4,704,116 A | 11/1987 | Enloe |
| 4,720,415 A | 1/1988 | Vander Wielen et al. |
| 4,766,029 A | 8/1988 | Brock et al. |
| 4,787,699 A | 11/1988 | Moulin |
| 4,789,592 A | 12/1988 | Taniguchi et al. |
| 4,795,668 A | 1/1989 | Krueger et al. |
| 4,798,603 A | 1/1989 | Meyer et al. |
| 4,816,094 A | 3/1989 | Pomplun et al. |
| 4,834,738 A | 5/1989 | Kielpikowski et al. |
| 4,916,005 A | 4/1990 | Lippert et al. |
| 4,937,299 A | 6/1990 | Ewen et al. |
| 4,940,464 A | 7/1990 | Van Gompel et al. |
| 4,965,122 A | 10/1990 | Morman |
| 4,981,747 A | 1/1991 | Morman |
| 5,003,178 A | 3/1991 | Livesay |
| 5,057,368 A | 10/1991 | Largman et al. |
| 5,069,970 A | 12/1991 | Largman et al. |
| 5,093,422 A | 3/1992 | Himes |
| 5,108,820 A | 4/1992 | Kaneko et al. |
| 5,140,757 A | 8/1992 | Terada |
| 5,162,074 A | 11/1992 | Hills |
| 5,169,706 A | 12/1992 | Collier, IV et al. |
| 5,176,668 A | 1/1993 | Bernardin |
| 5,176,672 A | 1/1993 | Bruemmer et al. |
| 5,192,606 A | 3/1993 | Proxmire et al. |
| 5,213,881 A | 5/1993 | Timmons et al. |
| 5,218,071 A | 6/1993 | Tsutsui et al. |
| 5,226,992 A | 7/1993 | Morman |
| 5,272,236 A | 12/1993 | Lai et al. |
| 5,277,976 A | 1/1994 | Hogle et al. |
| 5,278,272 A | 1/1994 | Lai et al. |
| 5,284,703 A | 2/1994 | Everhart et al. |
| 5,304,599 A | 4/1994 | Himes |
| 5,322,728 A | 6/1994 | Davey et al. |
| 5,332,613 A | 7/1994 | Taylor et al. |
| 5,336,545 A | 8/1994 | Morman |
| 5,336,552 A | 8/1994 | Strack et al. |
| 5,340,431 A | 8/1994 | Terada |
| 5,368,666 A | 11/1994 | Terada |
| 5,382,400 A | 1/1995 | Pike et al. |
| 5,385,775 A | 1/1995 | Wright |
| 5,399,219 A | 3/1995 | Roessler et al. |
| 5,429,856 A | 7/1995 | Krueger et al. |
| 5,464,688 A | 11/1995 | Timmons et al. |
| 5,466,410 A | 11/1995 | Hills |
| 5,472,775 A | 12/1995 | Obijeski et al. |
| 5,486,166 A | 1/1996 | Bishop et al. |
| 5,490,846 A | 2/1996 | Ellis et al. |
| 5,501,679 A | 3/1996 | Krueger et al. |
| 5,509,915 A | 4/1996 | Hanson et al. |
| 5,539,056 A | 7/1996 | Yang et al. |
| 5,540,796 A | 7/1996 | Fries |
| 5,560,793 A * | 10/1996 | Ruscher et al. ............... 156/73.1 |
| 5,571,619 A | 11/1996 | McAlpin et al. |
| 5,595,618 A | 1/1997 | Fries et al. |
| 5,596,052 A | 1/1997 | Resconi et al. |
| 5,620,780 A | 4/1997 | Krueger et al. |
| 5,649,916 A | 7/1997 | DiPalma et al. |
| 5,691,034 A | 11/1997 | Krueger et al. |
| 5,766,389 A | 6/1998 | Brandon et al. |
| 5,773,374 A | 6/1998 | Wood et al. |
| 5,800,903 A | 9/1998 | Wood et al. |
| 5,827,259 A | 10/1998 | Laux et al. |
| 5,840,412 A | 11/1998 | Wood et al. |
| 5,885,908 A | 3/1999 | Jaeger et al. |
| 5,932,497 A | 8/1999 | Morman et al. |
| H1808 H | 10/1999 | Djiauw et al. |
| 5,997,981 A | 12/1999 | McCormack et al. |
| 6,015,764 A | 1/2000 | McCormack et al. |
| 6,060,009 A | 5/2000 | Welygan et al. |
| 6,090,325 A | 7/2000 | Wheat et al. |
| 6,110,158 A | 8/2000 | Kielpikowski |
| 6,111,163 A | 8/2000 | McCormack et al. |
| 6,200,669 B1 | 3/2001 | Marmon et al. |
| 6,315,864 B2 | 11/2001 | Anderson et al. |
| 6,407,492 B1 | 6/2002 | Avnery et al. |
| 6,436,529 B1 | 8/2002 | Deeb et al. |
| 6,461,457 B1 | 10/2002 | Taylor et al. |
| 6,479,154 B1 | 11/2002 | Walton et al. |
| 6,500,563 B1 | 12/2002 | Datta et al. |
| 6,645,190 B1 | 11/2003 | Olson et al. |
| 6,663,611 B2 | 12/2003 | Blaney et al. |
| 6,667,351 B2 | 12/2003 | Langohr et al. |
| H2096 H | 1/2004 | Erderly et al. |
| 6,709,742 B2 | 3/2004 | Ladika et al. |
| 6,736,917 B2 | 5/2004 | Tange |
| 6,761,711 B1 | 7/2004 | Fletcher et al. |
| 6,794,024 B1 | 9/2004 | Walton et al. |
| 6,815,864 B2 | 11/2004 | Tanaka et al. |
| 6,824,734 B2 | 11/2004 | Boggs et al. |
| 6,902,796 B2 | 6/2005 | Morell et al. |
| 6,916,750 B2 | 7/2005 | Thomas et al. |
| 6,946,413 B2 | 9/2005 | Lange et al. |
| 6,964,720 B2 | 11/2005 | Schneider et al. |
| 2002/0009940 A1 | 1/2002 | May et al. |
| 2002/0049269 A1 | 4/2002 | Ho et al. |
| 2002/0104608 A1 | 8/2002 | Welch et al. |
| 2003/0068951 A1 | 4/2003 | Boggs et al. |
| 2004/0006324 A1 | 1/2004 | Zhou et al. |
| 2004/0110442 A1 | 6/2004 | Rhim et al. |
| 2004/0121687 A1 | 6/2004 | Morman et al. |
| 2004/0127131 A1 | 7/2004 | Potnis |
| 2005/0043460 A1 | 2/2005 | McCormack et al. |
| 2005/0148263 A1 | 7/2005 | Zhou et al. |
| 2005/0170729 A1 | 8/2005 | Stadelman et al. |
| 2005/0245162 A1 | 11/2005 | McCormack et al. |
| 2006/0003658 A1 | 1/2006 | Hall et al. |
| 2006/0055089 A1 | 3/2006 | Zhang et al. |
| 2006/0131783 A1 | 6/2006 | Morman et al. |
| 2006/0135024 A1 | 6/2006 | Thomas et al. |
| 2006/0148358 A1 | 7/2006 | Hall et al. |
| 2006/0151914 A1 | 7/2006 | Gerndt et al. |
| 2006/0246803 A1 | 11/2006 | Smith et al. |
| 2006/0251858 A1 | 11/2006 | Thomas et al. |

FOREIGN PATENT DOCUMENTS

| | | |
|---|---|---|
| WO | WO 9516425 A1 | 6/1995 |
| WO | WO 0039201 | 7/2000 |
| WO | WO 0132116 A1 | 5/2001 |
| WO | WO 03031151 A1 | 4/2003 |
| WO | WO 03040442 A1 | 5/2003 |
| WO | WO 2004 020174 A1 | 3/2004 |
| WO | WO 2004/031292 A2 * | 4/2004 |
| WO | WO 2005021262 A1 | 3/2005 |
| WO | WO 2005110719 A1 | 11/2005 |
| WO | WO 2007 070146 A1 | 6/2007 |

OTHER PUBLICATIONS

Product Data Sheet—EXACT 5361 Plastomer for Polymer Modification—Exxon Mobil Chemical.

ASTM D 5035-95, *Breaking Force and Elongation of Textile Fabrics (Strip Method)*.

ASTM D 3418-03, *Transition Temperatures and Enthalpies of Fusion and Crystallization of Polymers by Differential Scanning Calorimetry*.

ASTM D 1525-07, *Vicat Softening Temperature of Plastics*.
ASTM D 1505-03, *Density of Plastics by the Density-Gradient Technique*.
ASTM E 96-80, *Water Vapor Transmission of Materials*.
ASTM D 1238-01, *Melt Flow Rates of Thermoplastics by Extrusion Plastometer*.

ASTM D 2838-02, *Shrink Tension and Orientation Release Stress of Plastic Film and Thin Sheeting*.
Search Report and Written Opinion for PCT/IB2007/051132, Oct. 2, 2007.

* cited by examiner

STRAND COMPOSITE HAVING LATENT ELASTICITY

BACKGROUND OF THE INVENTION

Elastic composites are commonly incorporated into products (e.g., diapers, training pants, garments, etc.) to improve their ability to better fit the contours of the body. For example, the elastic composite may be formed from elastic strands and one or more nonwoven web facings. The nonwoven web facing may be joined to the strands while in a stretched condition so that the nonwoven web facing can gather between the locations where it is bonded to the strands when they are relaxed. The resulting elastic composite is stretchable to the extent that the nonwoven web facing gathered between the bond locations allows the elastic strands to elongate. Examples of stretch bonded composites are disclosed, for example, in U.S. Pat. No. 5,385,775 to Wright. Unfortunately, however, the stretchable nature of the composites may cause problems during the manufacturing process of the ultimate products. For example, the force required to unwind the rolled composites may at least partially extend the elastic composite while the elastic article is in tension. This partial extension of the stretchable composite can make it difficult to properly measure and position the desired quantity of the elastic article in the final product.

As such, a need exists for materials that remain relatively inelastic prior to incorporation into a final product, but which achieve a certain level of elasticity after having been activated in the final product.

SUMMARY OF THE INVENTION

In accordance with one embodiment of the present invention, a method of forming a nonwoven composite having latent elasticity is disclosed. The method comprises forming an elastic strand layer comprising a plurality of elastic strands, wherein the elastic strand layer is formed from a thermoplastic elastomer and semi-crystalline polyolefin. The elastic strand layer is stretched in the machine direction at a stretch ratio from about 2.0 to about 8.0, thereby forming a stretched elastic strand layer. The stretched elastic strand layer is allowed to relax to achieve a relaxation percentage of about 10% or more. A nonwoven web facing is laminated to the relaxed elastic strand layer.

In accordance with another embodiment of the present invention, a nonwoven composite having latent elasticity is disclosed. The composite comprises an elastic strand layer laminated to a nonwoven web facing. The elastic strand layer comprises a plurality of elastic strands and is formed from at least one thermoplastic elastomer and at least one semi-crystalline polyolefin. The semi-crystalline polyolefin constitutes from about 40 wt. % to about 95 wt. % of the elastic strand layer and the thermoplastic elastomer constitutes from about 5 wt. % to about 60 wt. % of the elastic strand layer. The composite exhibits a percent strain of about 50% or less when subjected to a load of 2000 grams-force per 3 inches wide in the machine direction prior to heat activation.

In accordance with still another embodiment of the present invention, a method for forming an absorbent article is disclosed. The method comprises fastening a nonwoven composite, such as described above, to one or more components of the article. The nonwoven composite is heated and allowed to retract, thereby increasing the stretchability of the composite.

Other features and aspects of the present invention are described in more detail below.

BRIEF DESCRIPTION OF THE DRAWINGS

A full and enabling disclosure of the present invention, including the best mode thereof, directed to one of ordinary skill in the art, is set forth more particularly in the remainder of the specification, which makes reference to the appended figures in which.

Figure 1:
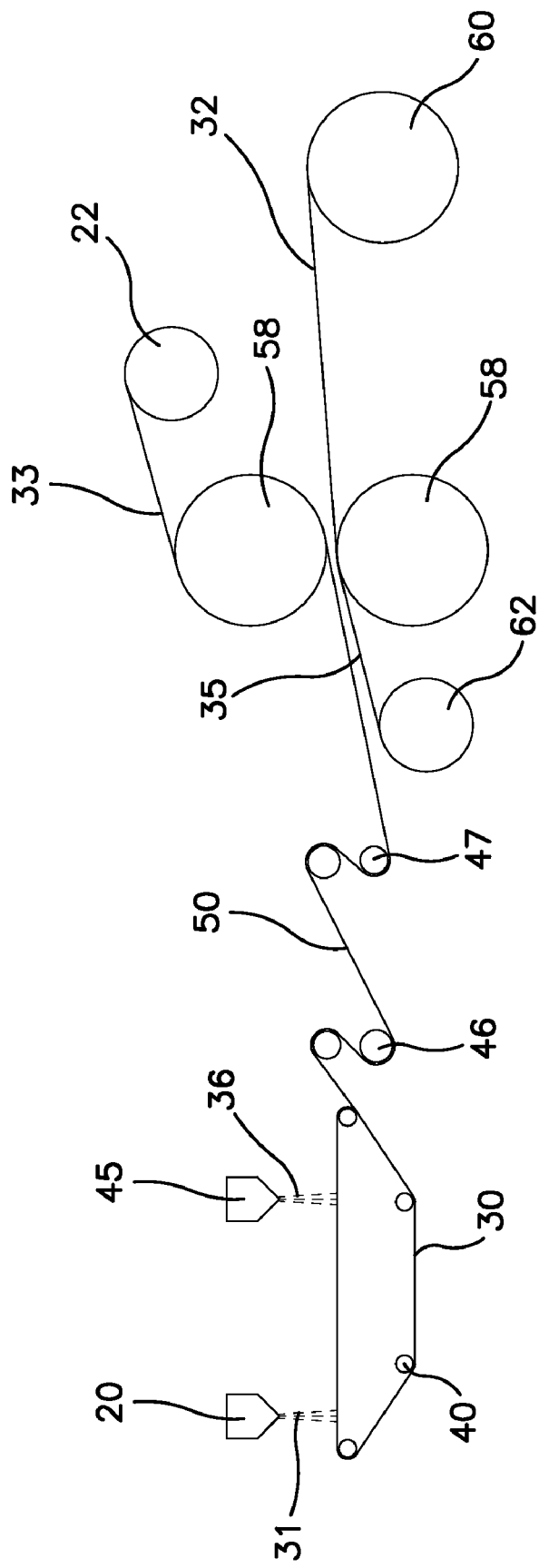
FIG. 1 schematically illustrates a method for forming a composite according to one embodiment of the present invention.

Repeat use of reference characters in the present specification and drawings is intended to represent same or analogous features or elements of the invention.

DETAILED DESCRIPTION OF REPRESENTATIVE EMBODIMENTS

Definitions

As used herein, the term "nonwoven web" generally refers to a web having a structure of individual fibers or threads which are interlaid, but not in an identifiable manner as in a knitted fabric. Examples of suitable nonwoven fabrics or webs include, but are not limited to, meltblown webs, spunbond webs, carded webs, etc. The basis weight of the nonwoven web may generally vary, such as from about 0.1 grams per square meter ("gsm") to 120 gsm, in some embodiments from about 0.5 gsm to about 70 gsm, and in some embodiments, from about 1 gsm to about 35 gsm.

As used herein, the term "meltblown web" generally refers to a nonwoven web that is formed by a process in which a molten thermoplastic material is extruded through a plurality of fine, usually circular, die capillaries as molten fibers into converging high velocity gas (e.g. air) streams that attenuate the fibers of molten thermoplastic material to reduce their diameter, which may be to microfiber diameter. Thereafter, the meltblown fibers are carried by the high velocity gas stream and are deposited on a collecting surface to form a web of randomly dispersed meltblown fibers. Such a process is disclosed, for example, in U.S. Pat. No. 3,849,241 to Butin, et al., which is incorporated herein in its entirety by reference thereto for all purposes. Generally speaking, meltblown fibers may be microfibers that are substantially continuous or discontinuous, generally smaller than 10 microns in diameter, and generally tacky when deposited onto a collecting surface.

As used herein, the term "spunbond web" generally refers to a web containing small diameter substantially continuous fibers. The fibers are formed by extruding a molten thermoplastic material from a plurality of fine, usually circular, capillaries of a spinnerette with the diameter of the extruded fibers then being rapidly reduced as by, for example, eductive drawing and/or other well-known spunbonding mechanisms. The production of spunbond webs is described and illustrated, for example, in U.S. Pat. No. 4,340,563 to Appel, et al., U.S. Pat. No. 3,692,618 to Dorschner. et al., U.S. Pat. No. 3,802,817 to Matsuki, et al., U.S. Pat. No. 3,338,992 to Kinney, U.S. Pat. No. 3,341,394 to Kinney, U.S. Pat. No. 3,502,763 to Hartman, U.S. Pat. No. 3,502,538 to Levy, U.S. Pat.

No. 3,542,615 to Dobo, et al., and U.S. Pat. No. 5,382,400 to Pike, et al., which are incorporated herein in their entirety by reference thereto for all purposes. Spunbond fibers are generally not tacky when they are deposited onto a collecting surface. Spunbond fibers may sometimes have diameters less than about 40 microns, and are often between about 5 to about 20 microns.

As used herein, the terms "machine direction" or "MD" generally refers to the direction in which a material is produced. The term "cross-machine direction" or "CD" refers to the direction perpendicular to the machine direction. Dimensions measured in the cross-machine direction are referred to as "width" dimension, while dimensions measured in the machine direction are referred to as "length" dimensions.

As used herein, the term "elastomeric" and "elastic" and refers to a material that, upon application of a stretching force, is stretchable in at least one direction (such as the CD direction), and which upon release of the stretching force, contracts/returns to approximately its original dimension. For example, a stretched material may have a stretched length that is at least 50% greater than its relaxed unstretched length, and which will recover to within at least 50% of its stretched length upon release of the stretching force. A hypothetical example would be a one (1) inch sample of a material that is stretchable to at least 1.50 inches and which, upon release of the stretching force, will recover to a length of not more than 1.25 inches. Desirably, the material contracts or recovers at least 50%, and even more desirably, at least 80% of the stretched length.

As used herein the terms "extensible" or "extensibility" generally refers to a material that stretches or extends in the direction of an applied force by at least about 50% of its relaxed length or width. An extensible material does not necessarily have recovery properties. For example, an elastomeric material is an extensible material having recovery properties. A meltblown web may be extensible, but not have recovery properties, and thus, be an extensible, non-elastic material.

As used herein, the term "set" refers to retained elongation in a material sample following the elongation and recovery, i.e., after the material has been stretched and allowed to relax during a cycle test.

As used herein, the term "percent set" is the measure of the amount of the material stretched from its original length after being cycled (the immediate deformation following the cycle test). The percent set is where the retraction curve of a cycle crosses the elongation axis. The remaining strain after the removal of the applied stress is measured as the percent set.

As used herein, the term "percent stretch" refers to the degree to which a material stretches in a given direction when subjected to a certain force. In particular, percent stretch is determined by measuring the increase in length of the material in the stretched dimension, dividing that value by the original dimension of the material, and then multiplying by 100. Such measurements are determined using the "strip elongation test", which is substantially in accordance with the specifications of ASTM D5035-95. Specifically, the test uses two clamps, each having two jaws with each jaw having a facing in contact with the sample. The clamps hold the material in the same plane, usually vertically, separated by 3 inches and move apart at a specified rate of extension. The sample size is 3 inches by 6 inches, with a jaw facing height of 1 inch and width of 3 inches, and a constant rate of extension of 300 mm/min. The specimen is clamped in, for example, a Sintech 2/S tester with a Renew MTS mongoose box (control) and using TESTWORKS 4.07b software (Sintech Corp, of Cary, N.C.). The test is conducted under ambient conditions.

As used herein, the "hysteresis value" of a sample may be determined by first elongating the sample ("load up") and then allowing the sample to retract ("load down"). The hysteresis value is the loss of energy during this cyclic loading.

DETAILED DESCRIPTION

Reference now will be made in detail to various embodiments of the invention, one or more examples of which are set forth below. Each example is provided by way of explanation, not limitation of the invention. In fact, it will be apparent to those skilled in the art that various modifications and variations may be made in the present invention without departing from the scope or spirit of the invention. For instance, features illustrated or described as part of one embodiment, may be used on another embodiment to yield a still further embodiment. Thus, it is intended that the present invention cover such modifications and variations.

Generally speaking, the present invention is directed to a nonwoven composite that exhibits latent elastic properties. The composite is formed from an elastic strand layer laminated to a nonwoven web facing. Latent elasticity may be imparted to the elastic strand layer through the combination of a thermoplastic elastomer and a polyolefin capable of forming semi-crystalline domains among the elastomeric chains. More specifically, the elastic strand layer may be stretched in one or more directions to orient the elastomer chains. Without intending to be limited by theory, the present inventors believe that the oriented state of the chains may be held in place by the relatively stiff semi-crystalline domains of the polyolefin. The stretched elastic strand layer may subsequently be relaxed and bonded to a nonwoven web facing to form the composite. The composite may be later activated (e.g., heated) to shrink the elastic strand layer and provide it with "latent" stretchability. For instance, the composite may be heated at or above the softening temperature of the polyolefin to soften the crystalline domains and allow the chains to return to their unoriented state. As a result of the present invention, the elastic strand layer may be extended and recover from its unoriented state.

I. Elastic Strand Layer

The elastic strand layer of the present invention generally contains a plurality of elastic strands. The number of strands may vary as desired, such as from 5 to about 20, in some embodiments from about 7 to about 18, and in some embodiments, from about 8 to 15 strands per cross-directional inch. The strands may have a circular cross-section, but may alternatively have other cross-sectional geometries such as elliptical, rectangular as in ribbon-like strands, triangular, multi-lobal, etc. The diameter of the strands (the widest cross-sectional dimension) may vary as desired, such as within a range of from 0.1 to about 4 millimeters, in some embodiments from about 0.2 to about 2.5 millimeters, and in some embodiments, from 0.5 to about 2 millimeters. Further, the elastic strands may generally be arranged in any direction or pattern. For example, in one embodiment, the strands are arranged in a direction that is substantially parallel to the machine direction and are desirably spaced apart from each other across the cross machine direction at similar intervals.

If desired, the elastic strands may be substantially continuous in length so that they are in the form of filaments. Such filaments may be produced using any of a variety of known techniques, such as by extruding an elastomeric polymeric composition from a die having a series of extrusion capillaries arranged in a row. As is well known in the art, meltblown dies may be suitable for forming the filaments, except that the high velocity gas streams used in fiber attenuation are generally not employed. Rather, the molten polymer extrudate is pumped from the die capillaries and allowed to extend away from the die under the impetus of gravity. Besides extruded filaments, other elastic filaments may also be employed in the present invention, such as the spandex-type materials available under the designation "LYCRA®" from Invista North America of Wilmington, Del.

Regardless of the particular configuration of the strands, the elastic strand layer of the present invention employs a combination of a thermoplastic elastomer and a semi-crystalline polyolefin. Any of a variety of thermoplastic elastomers may generally be employed, such as elastomeric polyesters, elastomeric polyurethanes, elastomeric polyamides, elastomeric copolymers, and so forth, may be employed in some embodiments of the present invention. For example, the thermoplastic elastomer may be a substantially amorphous block copolymer having at least two blocks of a monoalkenyl arene polymer separated by at least one block of a saturated conjugated diene polymer. The monoalkenyl arene blocks may include styrene and its analogues and homologues, such as o-methyl styrene; p-methyl styrene; p-tert-butyl styrene; 1,3 dimethyl styrene p-methyl styrene; etc., as well as other monoalkenyl polycyclic aromatic compounds, such as vinyl naphthalene; vinyl anthrycene; and so forth. Preferred monoalkenyl arenes are styrene and p-methyl styrene. The conjugated diene blocks may include homopolymers of conjugated diene monomers, copolymers of two or more conjugated dienes, and copolymers of one or more of the dienes with another monomer in which the blocks are predominantly conjugated diene units. Preferably, the conjugated dienes contain from 4 to 8 carbon atoms, such as 1,3 butadiene (butadiene); 2-methyl-1,3 butadiene; isoprene; 2,3 dimethyl-1,3 butadiene; 1,3 pentadiene (piperylene); 1,3 hexadiene; and so forth.

The amount of monoalkenyl arene (e.g., polystyrene) blocks may vary, but typically constitute from about 8 wt. % to about 55 wt. %, in some embodiments from about 10 wt. % to about 35 wt. %, and in some embodiments, from about 25 wt. % to about 35 wt. % of the copolymer. Suitable block copolymers may contain monoalkenyl arene endblocks having a number average molecular weight from about 5,000 to about 35,000 and saturated conjugated diene midblocks having a number average molecular weight from about 20,000 to about 170,000. The total number average molecular weight of the block polymer may be from about 30,000 to about 250,000.

Particularly suitable thermoplastic elastomers are available from Kraton Polymers LLC of Houston, Tex. under the trade name KRATON®. KRATON® polymers include styrene-diene block copolymers, such as styrene-butadiene, styrene-isoprene, styrene-butadiene-styrene, and styrene-isoprene-styrene. KRATON® polymers also include styrene-olefin block copolymers formed by selective hydrogenation of styrene-diene block copolymers. Examples of such styrene-olefin block copolymers include styrene-(ethylene-butylene), styrene-(ethylene-propylene), styrene-(ethylene-butylene)-styrene, styrene-(ethylene-propylene)-styrene, styrene-(ethylene-butylene)-styrene-(ethylene-butylene), styrene-(ethylene-propylene)-styrene-(ethylene-propylene), and styrene-ethylene-(ethylene-propylene)-styrene. These block copolymers may have a linear, radial or star-shaped molecular configuration. Specific KRATON® block copolymers include those sold under the brand names G 1652, G 1657, G 1730, MD6673, and MD6937. Various suitable styrenic block copolymers are described in U.S. Pat. Nos. 4,663,220, 4,323,534, 4,834,738, 5,093,422 and 5,304,599, which are hereby incorporated in their entirety by reference thereto for all purposes. Other commercially available block copolymers include the S-EP-S elastomeric copolymers available from Kuraray Company, Ltd. of Okayama, Japan, under the trade designation SEPTON®. Still other suitable copolymers include the S-I-S and S-B-S elastomeric copolymers available from Dexco Polymers of Houston, Tex. under the trade designation VECTOR®. Also suitable are polymers composed of an A-B-A-B tetrablock copolymer, such as discussed in U.S. Pat. No. 5,332,613 to Taylor, et al., which is incorporated herein in its entirety by reference thereto for all purposes. An example of such a tetrablock copolymer is a styrene-poly(ethylene-propylene)-styrene-poly(ethylene-propylene) ("S-EP-S-EP") block copolymer.

Other exemplary thermoplastic elastomers that may be used include polyurethane elastomeric materials such as, for example, those available under the trademark ESTANE from Noveon and LYCRA from Invista, polyamide elastomeric materials such as, for example, those available under the trademark PEBAX (polyether amide) from Atofina Chemicals Inc., of Philadelphia, Pa., and polyester elastomeric materials such as, for example, those available under the trade designation HYTREL from E.I. DuPont De Nemours & Company.

The semi-crystalline polyolefin of the elastic strand layer has or is capable of exhibiting a substantially regular structure. That is, semi-crystalline polyolefins may be substantially amorphous in their undeformed state, but form crystalline domains upon stretching. The degree of crystallinity of the olefin polymer may be from about 3% to about 30%, in some embodiments from about 5% to about 25%, and in some embodiments, from about 5% and about 15%. Likewise, the semi-crystalline polyolefin may have a latent heat of fusion ($\Delta H_f$), which is another indicator of the degree of crystallinity, of from about 15 to about 75 Joules per gram ("J/g"), in some embodiments from about 20 to about 65 J/g, and in some embodiments, from 25 to about 50 J/g. The semi-crystalline polyolefin may also have a Vicat softening temperature of from about 10° C. to about 100° C., in some embodiments from about 20° C. to about 80° C., and in some embodiments, from about 30° C. to about 60° C. The semi-crystalline polyolefin may have a melting temperature of from about 20° C. to about 120° C., in some embodiments from about 35° C. to about 90° C., and in some embodiments, from about 40° C. to about 80° C. The latent heat of fusion ($\Delta H_f$) and melting temperature may be determined using differential scanning calorimetry ("DSC") in accordance with ASTM D-3417 as is well known to those skilled in the art. The Vicat softening temperature may be determined in accordance with ASTM D-1525.

Exemplary semi-crystalline polyolefins include polyethylene, polypropylene, blends and copolymers thereof. In one particular embodiment, a polyethylene is employed that is a copolymer of ethylene and an α-olefin, such as a $C_3$-$C_{20}$ α-olefin or $C_3$-$C_{12}$ α-olefin. Suitable α-olefins may be linear or branched (e.g., one or more $C_1$-$C_3$ alkyl branches, or an aryl group). Specific examples include 1-butene; 3-methyl-1-butene; 3,3-dimethyl-1-butene; 1-pentene; 1-pentene with one or more methyl, ethyl or propyl substituents; 1-hexene with one or more methyl, ethyl or propyl substituents; 1-heptene with one or more methyl, ethyl or propyl substituents; 1-octene with one or more methyl, ethyl or propyl substituents; 1-nonene with one or more methyl, ethyl or propyl substituents; ethyl, methyl or dimethyl-substituted 1-decene; 1-dodecene; and styrene. Particularly desired α-olefin comonomers are 1-butene, 1-hexene and 1-octene. The ethylene content of such copolymers may be from about 60 mole % to about 99 mole %, in some embodiments from about 80 mole % to about 98.5 mole %, and in some embodiments, from about 87 mole % to about 97.5 mole %. The α-olefin content may likewise range from about 1 mole % to about 40 mole %, in some embodiments from about 1.5 mole % to about 15 mole %, and in some embodiments, from about 2.5 mole % to about 13 mole %.

The density of the polyethylene may vary depending on the type of polymer employed, but generally ranges from 0.85 to 0.96 grams per cubic centimeter ("g/cm$^3$"). Polyethylene "plastomers", for instance, may have a density in the range of from 0.85 to 0.91 g/cm$^3$. Likewise, "linear low density polyethylene" ("LLDPE") may have a density in the range of from 0.91 to 0.940 g/cm$^3$; "low density polyethylene" ("LDPE") may have a density in the range of from 0.910 to 0.940 g/cm$^3$; and "high density polyethylene" ("HDPE") may have density in the range of from 0.940 to 0.960 g/cm$^3$. Densities may be measured in accordance with ASTM 1505.

Particularly suitable polyethylene copolymers are those that are "linear" or "substantially linear." The term "substantially linear" means that, in addition to the short chain branches attributable to comonomer incorporation, the ethylene polymer also contains long chain branches in the polymer backbone. "Long chain branching" refers to a chain length of at least 6 carbons. Each long chain branch may have the same comonomer distribution as the polymer backbone and be as long as the polymer backbone to which it is attached. Preferred substantially linear polymers are substituted with from 0.01 long chain branch per 1000 carbons to 1 long chain branch per 1000 carbons, and in some embodiments, from 0.05 long chain branch per 1000 carbons to 1 long chain branch per 1000 carbons. In contrast to the term "substantially linear", the term "linear" means that the polymer lacks measurable or demonstrable long chain branches. That is, the polymer is substituted with an average of less than 0.01 long chain branch per 1000 carbons.

The density of a linear ethylene/α-olefin copolymer is a function of both the length and amount of the α-olefin. That is, the greater the length of the α-olefin and the greater the amount of α-olefin present, the lower the density of the copolymer. Although not necessarily required, linear polyethylene "plastomers" are particularly desirable in that the content of α-olefin short chain branching content is such that the ethylene copolymer exhibits both plastic and elastomeric characteristics—i.e., a "plastomer." Because polymerization with α-olefin comonomers decreases crystallinity and density, the resulting plastomer normally has a density lower than that of polyethylene thermoplastic polymers (e.g., LLDPE), but approaching and/or overlapping that of an elastomer. For example, the density of the polyethylene plastomer may be about 0.91 grams per cubic centimeter (g/cm$^3$) or less, in some embodiments from about 0.85 to about 0.88 g/cm$^3$, and in some embodiments, from about 0.85 g/cm$^3$ to about 0.87 g/cm$^3$. Despite having a density similar to elastomers, plastomers generally exhibit a higher degree of crystallinity, are relatively non-tacky, and may be formed into pellets that are non-adhesive and relatively free flowing.

The distribution of the α-olefin comonomer within a polyethylene plastomer is typically random and uniform among the differing molecular weight fractions forming the ethylene copolymer. This uniformity of comonomer distribution within the plastomer may be expressed as a comonomer distribution breadth index value ("CDBI") of 60 or more, in some embodiments 80 or more, and in some embodiments, 90 or more. Further, the polyethylene plastomer may be characterized by a DSC melting point curve that exhibits the occurrence of a single melting point peak occurring in the region of 50 to 110° C. (second melt rundown).

Preferred plastomers for use in the present invention are ethylene-based copolymer plastomers available under the AFFINITY™ from Dow Chemical Company of Midland, Mich. Other suitable polyethylene plastomers are available under the designation ENGAGE™ from Dow Chemical Company of Midland, Mich. and EXACT™ from ExxonMobil Chemical Company of Houston, Tex. Still other suitable ethylene polymers are available from The Dow Chemical Company under the designations DOWLEX™ (LLDPE) and ATTANE™ (ULDPE). Other suitable ethylene polymers are described in U.S. Pat. No. 4,937,299 to Ewen et al.; U.S. Pat. No. 5,218,071 to Tsutsui et al.; U.S. Pat. No. 5,272,236 to Lai et al.; and U.S. Pat. No. 5,278,272 to Lai, et al., which are incorporated herein in their entirety by reference thereto for all purposes.

Of course, the present invention is by no means limited to the use of ethylene polymers. For instance, propylene polymers may also be suitable for use as a semi-crystalline polyolefin. In one particular embodiment, the semi-crystalline propylene-based polymer includes a copolymer of propylene and an α-olefin, such as a $C_2$-$C_{20}$ α-olefin or $C_2$-$C_{12}$ α-olefin. Particularly desired α-olefin comonomers are ethylene, 1-butene, 1-hexene and 1-octene. The propylene content of such copolymers may be from about 60 mole % to about 99.5 wt. %, in some embodiments from about 80 mole % to about 99 mole %, and in some embodiments, from about 85 mole % to about 98 mole %. The α-olefin content may likewise range from about 0.5 mole % to about 40 mole %, in some embodiments from about 1 mole % to about 20 mole %, and in some embodiments, from about 2 mole % to about 15 mole %. The distribution of the α-olefin comonomer is typically random and uniform among the differing molecular weight fractions forming the propylene copolymer. Although the density of the propylene-based polymer employed in the present invention may vary, it is typically about 0.91 grams per cubic centimeter (g/cm$^3$) or less, in some embodiments from about 0.85 to about 0.88 g/cm$^3$, and in some embodiments, from about 0.85 g/cm$^3$ to about 0.87 g/cm$^3$. The melt flow rate of the propylene-based polymer may also be selected within a certain range to optimize the properties of the resulting elastic material. The melt flow rate is the weight of a polymer (in grams) that may be forced through an extrusion rheometer orifice (0.0825-inch diameter) when subjected to a force of 2160 grams in 10 minutes at 230° C. Generally speaking, the melt flow rate is high enough to improve melt processability, but not so high as to adversely interfere with binding properties. Thus, in most embodiments of the present invention, the propylene-based polymer has a melt flow index of from about 0.1 to about 10 grams per 10 minutes, in some embodiments from about 0.2 to about 5 grams per 10 minutes, and in some embodiments, from about 0.5 to about 4 grams per 10 minutes, measured in accordance with ASTM Test Method D1238-E.

Suitable propylene polymers are commercially available under the designations VISTAMAXX™ from ExxonMobil Chemical Co. of Houston, Tex.; FINA™ (e.g., 8573) from Atofina Chemicals of Feluy, Belgium; TAFMER™ available from Mitsui Petrochemical Industries; and VERSIFY™ available from Dow Chemical Co. of Midland, Mich. Other examples of suitable propylene polymers are described in U.S. Pat. No. 6,500,563 to Datta, et al.; U.S. Pat. No. 5,539,056 to Yang, et al.; and U.S. Pat. No. 5,596,052 to Resconi, et al., which are incorporated herein in their entirety by reference thereto for all purposes.

Any of a variety of known techniques may generally be employed to form the semi-crystalline polyolefins. For instance, olefin polymers may be formed using a free radical or a coordination catalyst (e.g., Ziegler-Natta). Preferably, the olefin polymer is formed from a single-site coordination catalyst, such as a metallocene catalyst. Such a catalyst system produces ethylene copolymers in which the comonomer is randomly distributed within a molecular chain and uniformly distributed across the different molecular weight fractions. Metallocene-catalyzed polyolefins are described, for instance, in U.S. Pat. No. 5,571,619 to McAlpin et al.; U.S. Pat. No. 5,322,728 to Davis et al.; U.S. Pat. No. 5,472,775 to Obijeski et al.; U.S. Pat. No. 5,272,236 to Lai et al.; and U.S. Pat. No. 6,090,325 to Wheat, et al., which are incorporated herein in their entirety by reference thereto for all purposes. Examples of metallocene catalysts include bis(n-butylcyclopentadienyl)titanium dichloride, bis(n-butylcyclopentadienyl)zirconium dichloride, bis(cyclopentadienyl)scandium chloride, bis(indenyl)zirconium dichloride, bis(methylcyclopentadienyl)titanium dichloride, bis(methylcyclopentadienyl)zirconium dichloride, cobaltocene, cyclopentadienyltitanium trichloride, ferrocene, hafnocene dichloride, isopropyl(cyclopentadienyl,-1-flourenyl)zirconium dichloride, molybdocene dichloride, nickelocene, niobocene dichloride, ruthenocene, titanocene dichloride, zirconocene chloride hydride, zirconocene dichloride, and so forth. Polymers made using metallocene catalysts typically have a narrow molecular weight range. For instance, metallocene-catalyzed polymers may have polydispersity numbers ($M_w/M_n$) of below 4, controlled short chain branching distribution, and controlled isotacticity.

The melt flow index (MI) of the semi-crystalline polyolefins may generally vary, but is typically in the range of about 0.1 grams per 10 minutes to about 100 grams per 10 minutes, in some embodiments from about 0.5 grams per 10 minutes to about 30 grams per 10 minutes, and in some embodiments, about 1 to about 10 grams per 10 minutes, determined at 190° C. The melt flow index is the weight of the polymer (in grams) that may be forced through an extrusion rheometer orifice (0.0825-inch diameter) when subjected to a force of 2.16 kilograms in 10 minutes at 190° C., and may be determined in accordance with ASTM Test Method D1238-E.

The relative amounts of the thermoplastic elastomers and semi-crystalline polyolefins are selectively controlled in accordance with the present invention to achieve a balance between the mechanical and thermal properties of the elastic strand layer. For example, the ratio of the amount of the thermoplastic elastomer(s) to the amount of the semi-crystalline polyolefin(s) may range from about 0.5 to about 15, in some embodiments from about 1 to about 10, and in some embodiments, from about 1 to about 5. The thermoplastic elastomer(s) may constitute from about 40 wt. % to about 95 wt. %, in some embodiments from about 45 wt. % to about 90 wt. %, and in some embodiments, from about 50 wt. % to about 75 wt. % of the elastic strand layer. Likewise, the semi-crystalline polyolefin(s) may constitute from about 5 wt. % to about 60 wt. %, in some embodiments from about 10 wt. % to about 55 wt. %, and in some embodiments, from about 15 wt. % to about 50 wt. % of the elastic strand layer. It should of course be understood that other polymers may also be employed in the elastic strand layer. When utilized, however, the other polymers typically constitute about 10 wt. % or less, and in some embodiments, about 5 wt. % or less of the material.

In addition to polymers, the elastic strand layer may also employ other additives as is known in the art. For example, although the elastomeric polymers may possess a certain amount of tack, a tackifying resin may nevertheless be employed in some embodiments to facilitate subsequent bonding of the strand layer to a nonwoven web facing. One suitable class of tackifying resins includes hydrogenated hydrocarbon resins, such as REGALREZ™ hydrocarbon resins available from Eastman Chemical. Other suitable tackifying resins may be described in U.S. Pat. No. 4,787,699. When employed, the tackifying resin may be present in an amount from about 0.001 wt. % to about 35 wt. %, in some embodiments, from about 0.005 wt. % to about 30 wt. %, and in some embodiments, from 0.01 wt. % to about 25 wt. % of the elastic strand layer.

The elastic strand layer may also contain other additives as is known in the art, such as melt stabilizers, processing stabilizers, heat stabilizers, light stabilizers, antioxidants, heat aging stabilizers, whitening agents, antiblocking agents, bonding agents, viscosity modifiers, etc. Viscosity modifiers may also be employed, such as polyethylene wax (e.g., EPOLENE™ C-10 from Eastman Chemical). Phosphite stabilizers (e.g., IRGAFOS available from Ciba Specialty Chemicals of Terrytown, N.Y. and DOVERPHOS available from Dover Chemical Corp. of Dover, Ohio) are exemplary melt stabilizers. In addition, hindered amine stabilizers (e.g., CHIMASSORB available from Ciba Specialty Chemicals) are exemplary heat and light stabilizers. Further, hindered phenols are commonly used as an antioxidant in the production of fibers and films. Some suitable hindered phenols include those available from Ciba Specialty Chemicals of under the trade name "Irganox®", such as Irganox® 1076, 1010, or E 201. Moreover, bonding agents may also be added to facilitate bonding to additional materials (e.g., nonwoven web). When employed, additives (e.g., antioxidant, stabilizer, etc.) may each be present in an amount from about 0.001 wt. % to about 40 wt. %, in some embodiments, from about 0.005 wt. % to about 35 wt. %, and in some embodiments, from 0.01 wt. % to about 25 wt. % of the elastic strand layer.

The elastic strand layer may be in the form of a single layer of strands or a laminate containing the strands. Depending on the particular configuration of the layer, the polymer content of the elastic strands and/or other components of the layer may be selected to provide the desired degree of latent elasticity to the composite. When used in a single layer, for example, the elastic strands may be formed from a blend of a thermoplastic elastomer and semi-crystalline polyolefin. In this embodiment, the thermoplastic elastomer(s) may constitute from about 40 wt. % to about 95 wt. %, in some embodiments from about 45 wt. % to about 90 wt. %, and in some embodiments, from about 50 wt. % to about 75 wt. % of the strands. Likewise, the semi-crystalline polyolefin(s) may constitute from about 5 wt. % to about 60 wt. %, in some embodiments from about 10 wt. % to about 55 wt. %, and in some embodiments, from about 15 wt. % to about 50 wt. % of the strands.

In other embodiments of the present invention, the elastic strand layer is a laminate that includes multiple layers. For example, the laminate may contain strands laminated to a meltblown web to help secure the strands to a facing so that they are less likely to loosen during use. Examples of such laminates are described in more detail, for instance, in U.S. Pat. No. 5,385,775 to Wright and U.S. Patent Application Publication No. 2005/0170729 to Stadelman. et al., which are incorporated herein in their entirety by reference thereto for all purposes. The strands and the meltblown web may contain a thermoplastic elastomer, semi-crystalline polyolefin, or combinations thereof. In one embodiment, the strands contain a thermoplastic elastomer and the meltblown web contains a semi-crystalline polyolefin. For example, the thermoplastic elastomer(s) may constitute about 70 wt. % or more, in some embodiments about 80 wt. % or more, and in some embodiments, about 90 wt. % or more of the strands, while the semi-crystalline polyolefin(s) may constitute about 70 wt. % or more, in some embodiments about 80 wt. % or more, and in some embodiments, about 90 wt. % or more of the meltblown web. In this manner, the relatively stiff semi-crystalline domains of the meltblown web may hold the elastomeric chains of the strands in an oriented state (when stretched). Upon subsequent heat activation, the semi-crystalline domains may be softened and release oriented chains to impart latent elasticity to the composite.

Even when the meltblown web is formed from an elastomeric polymer, such as described above, it is normally desired that the basis weight (or add-on level) of the strands is greater than the meltblown web to optimize the elasticity of the composite. However, too high of a strand basis weight relative to the meltblown web basis weight may result in a composite lacking the desired latency characteristics. Thus, the ratio of the strand basis weight to the meltblown web basis weight is typically from about 1.2 to about 5.0, in some embodiments from about 1.5 to about 4.0, and in some embodiments, from about 2.0 to about 3.5. The basis weight of the meltblown layer (after stretching) may range from about 0.1 to about 30 gram per square meter ("gsm"), in some embodiments about 0.5 to about 20 gsm, and in some embodiments, from about 1 to about 15 gsm. Likewise, the basis weight of the strands (after stretching) may range from about 1 to about 75 gsm, in some embodiments from about 4 to about 60 gsm, and in some embodiments, from about 5 to about 40 gsm.

Regardless of the particular manner in which it is formed, the elastic strand layer of the present invention exhibits good latent stretch properties for use in a wide variety of applications. One measurement that is indicative of the latent stretch properties of the material is the heat shrinkage performance, which is a measure of recoverable deformation upon activation. A very high level of heat shrinkage may be achieved in the present invention, such as about 40% or more, in some embodiments about 50% or more, and in some embodiments, about 60% or more. As described in the "Test Methods" below, heat shrinkage is determined by heating the material in water at 160° F. for 30 seconds to 1 minute. Alternatively, shrinkage may be determined using ASTM D2838-02. Any known method of activation may generally be employed in the present invention, including the application of heat, radiation (e.g., microwave), as well as chemical or mechanical treatments. Heat activation may be accomplished at temperatures of from about 50° C. to about 100° C., in some embodiments from about 60° C. to about 90° C., and in some embodiments, from about 70° C. to about 80° C. Any of a variety of techniques may be used to apply heat to the elastic strand layer, such as heated rolls, oven heating, and so forth.

II. Nonwoven Web Facing

A nonwoven web facing is generally employed in the present invention to reduce the coefficient of friction and enhance the cloth-like feel of the composite surface. Exemplary polymers for use in forming nonwoven web facings may include, for instance, polyolefins, e.g., polyethylene, polypropylene, polybutylene, etc.; polytetrafluoroethylene; polyesters, e.g., polyethylene terephthalate and so forth; polyvinyl acetate; polyvinyl chloride acetate; polyvinyl butyral; acrylic resins, e.g., polyacrylate, polymethylacrylate, polymethylmethacrylate, and so forth; polyamides, e.g., nylon; polyvinyl chloride; polyvinylidene chloride; polystyrene; polyvinyl alcohol; polyurethanes; polylactic acid; copolymers thereof; and so forth. If desired, biodegradable polymers, such as those described above, may also be employed. Synthetic or natural cellulosic polymers may also be used, including but not limited to, cellulosic esters; cellulosic ethers; cellulosic nitrates; cellulosic acetates; cellulosic acetate butyrates; ethyl cellulose; regenerated celluloses, such as viscose, rayon, and so forth. It should be noted that the polymer(s) may also contain other additives, such as processing aids or treatment compositions to impart desired properties to the fibers, residual amounts of solvents, pigments or colorants, and so forth.

Monocomponent and/or multicomponent fibers may be used to form the nonwoven web facing. Monocomponent fibers are generally formed from a polymer or blend of polymers extruded from a single extruder. Multicomponent fibers are generally formed from two or more polymers (e.g., bicomponent fibers) extruded from separate extruders. The polymers may be arranged in substantially constantly positioned distinct zones across the cross-section of the fibers. The components may be arranged in any desired configuration, such as sheath-core, side-by-side, pie, island-in-the-sea, three island, bull's eye, or various other arrangements known in the art. Various methods for forming multicomponent fibers are described in U.S. Pat. No. 4,789,592 to Taniguchi et al. and U.S. Pat. No. 5,336,552 to Strack et al., U.S. Pat. No. 5,108,820 to Kaneko, et al., U.S. Pat. No. 4,795,668 to Kruege, et al., U.S. Pat. No. 5,382,400 to Pike, et al., U.S. Pat. No. 5,336,552 to Strack, et al., and U.S. Pat. No. 6,200,669 to Marmon, et al., which are incorporated herein in their entirety by reference thereto for all purposes. Multicomponent fibers having various irregular shapes may also be formed, such as described in U.S. Pat. No. 5,277,976 to Hogle, et al., U.S. Pat. No. 5,162,074 to Hills, U.S. Pat. No. 5,466,410 to Hills, U.S. Pat. No. 5,069,970 to Largman, et al., and U.S. Pat. No. 5,057,368 to Largman, et al., which are incorporated herein in their entirety by reference thereto for all purposes.

Although any combination of polymers may be used, the polymers of the multicomponent fibers are typically made from thermoplastic materials with different glass transition or melting temperatures where a first component (e.g., sheath) melts at a temperature lower than a second component (e.g., core). Softening or melting of the first polymer component of the multicomponent fiber allows the multicomponent fibers to form a tacky skeletal structure, which upon cooling, stabilizes the fibrous structure. For example, the multicomponent fibers may have from about 20% to about 80%, and in some embodiments, from about 40% to about 60% by weight of the low melting polymer. Further, the multicomponent fibers may have from about 80% to about 20%, and in some embodiments, from about 60% to about 40%, by weight of the high melting polymer. Some examples of known sheath-core bicomponent fibers available from KoSa Inc. of Charlotte, N.C. under the designations T-255 and T-256, both of which use a polyolefin sheath, or T-254, which has a low melt co-polyester sheath. Still other known bicomponent fibers that may be used include those available from the Chisso Corporation of Moriyama, Japan or Fibervisions LLC of Wilmington, Del.

Fibers of any desired length may be employed, such as staple fibers, continuous fibers, etc. In one particular embodiment, for example, staple fibers may be used that have a fiber length in the range of from about 1 to about 150 millimeters, in some embodiments from about 5 to about 50 millimeters, in some embodiments from about 10 to about 40 millimeters, and in some embodiments, from about 10 to about 25 millimeters. Although not required, carding techniques may be employed to form fibrous layers with staple fibers as is well known in the art. For example, fibers may be formed into a carded web by placing bales of the fibers into a picker that separates the fibers. Next, the fibers are sent through a combing or carding unit that further breaks apart and aligns the fibers in the machine direction so as to form a machine direction-oriented fibrous nonwoven web. The carded web may then be bonded using known techniques to form a bonded carded nonwoven web.

If desired, the nonwoven web facing used to form the nonwoven composite may have a multi-layer structure. Suitable multi-layered materials may include, for instance, spunbond/meltblown/spunbond (SMS) laminates and spunbond/meltblown (SM) laminates. Various examples of suitable SMS laminates are described in U.S. Pat. No. 4,041,203 to Brock et al.; U.S. Pat. No. 5,213,881 to Timmons, et al.; U.S. Pat. No. 5,464,688 to Timmons, et al.; U.S. Pat. No. 4,374,888 to Bornslaeger; U.S. Pat. No. 5,169,706 to Collier, et al.; and U.S. Pat. No. 4,766,029 to Brock et al., which are incorporated herein in their entirety by reference thereto for all purposes. In addition, commercially available SMS laminates may be obtained from Kimberly-Clark Corporation under the designations Spunguard® and Evolution®.

Another example of a multi-layered structure is a spunbond web produced on a multiple spin bank machine in which a spin bank deposits fibers over a layer of fibers deposited from a previous spin bank. Such an individual spunbond nonwoven web may also be thought of as a multi-layered structure. In this situation, the various layers of deposited fibers in the nonwoven web may be the same, or they may be different in basis weight and/or in terms of the composition, type, size, level of crimp, and/or shape of the fibers produced. As another example, a single nonwoven web may be provided as two or more individually produced layers of a spunbond web, a carded web, etc., which have been bonded together to form the nonwoven web. These individually produced layers may differ in terms of production method, basis weight, composition, and fibers as discussed above.

A nonwoven web facing may also contain an additional fibrous component such that it is considered a composite. For example, a nonwoven web may be entangled with another fibrous component using any of a variety of entanglement techniques known in the art (e.g., hydraulic, air, mechanical, etc.). In one embodiment, the nonwoven web is integrally entangled with cellulosic fibers using hydraulic entanglement. A typical hydraulic entangling process utilizes high pressure jet streams of water to entangle fibers to form a highly entangled consolidated fibrous structure, e.g., a nonwoven web. Hydraulically entangled nonwoven webs of staple length and continuous fibers are disclosed, for example, in U.S. Pat. No. 3,494,821 to Evans and U.S. Pat. No. 4,144,370 to Boulton, which are incorporated herein in their entirety by reference thereto for all purposes. Hydraulically entangled composite nonwoven webs of a continuous fiber nonwoven web and a pulp layer are disclosed, for example, in U.S. Pat. No. 5,284,703 to Everhart, et al. and U.S. Pat. No. 6,315,864 to Anderson, et al., which are incorporated herein in their entirety by reference thereto for all purposes. The fibrous component of the composite may contain any desired amount of the resulting substrate. The fibrous component may contain greater than about 50% by weight of the composite, and in some embodiments, from about 60% to about 90% by weight of the composite. Likewise, the nonwoven web may contain less than about 50% by weight of the composite, and in some embodiments, from about 10% to about 40% by weight of the composite.

Although not required, the nonwoven web facing may be necked in one or more directions prior to lamination to the elastic strand layer of the present invention. Suitable necking techniques are described in U.S. Pat. Nos. 5,336,545, 5,226,992, 4,981,747 and 4,965,122 to Morman, as well as U.S. Patent Application Publication No. 2004/0121687 to Morman, et al. Alternatively, the nonwoven web may remain relatively inextensible in at least one direction prior to lamination to the elastic strand layer. In such embodiments, the nonwoven web may be optionally stretched in one or more directions subsequent to lamination to the elastic strand layer.

The basis weight of the nonwoven web facing may generally vary, such as from about 5 grams per square meter ("gsm") to 120 gsm, in some embodiments from about 8 gsm to about 70 gsm, and in some embodiments, from about 10 gsm to about 35 gsm. When multiple nonwoven web facings, such materials may have the same or different basis weights.

III. Lamination Technique

To achieve the desired latent elasticity of the composite, the elastic strand layer is initially stretched in one or more directions to orient the chains of the thermoplastic elastomer(s). Thereafter, the stretched material is relaxed to a certain degree and bonded to a nonwoven web facing. Because the elastic strand layer is in a relaxed stated during lamination, the nonwoven web facing does not gather to a significant extent. Thus, despite the fact that the composite contains an elastomeric polymer, its elastic properties are initially limited by the presence of the relatively inelastic nonwoven web facing. Upon heat activation, however, the semi-crystalline domains of the polyolefin may soften and release the chains from their oriented configuration. This causes the elastic strand layer to further shrink and thereby "gather" the nonwoven web facing. In this manner, the heat-activated composite is provided with latent elasticity.

In this regard, various embodiments of the lamination method will now be described in greater detail. Of course, it should be understood that the description provided below is merely exemplary, and that other methods are contemplated by the present invention. Referring to FIG. 1, for instance, one embodiment of a "horizontal" method for forming a continuous filament laminate is shown. As shown, a first extrusion apparatus 20 is fed with the raw materials (e.g., thermoplastic elastomer) used to form the continuous filaments. The materials may be dry mixed together (i.e., without a solvent) or alternatively blended with a solvent. In the hopper, the materials are dispersively mixed in the melt and compounded using any known technique, such as batch and/or continuous compounding techniques that employ, for example, a Banbury mixer, Farrel continuous mixer, single screw extruder, twin screw extruder, etc. The first extrusion apparatus 20 extrudes the raw materials in the form of filaments 31 onto a forming surface 30 (e.g., a foraminous belt) moving clockwise about rolls 40. A vacuum (not shown) may also help hold the filaments 31 against the forming surface 30. In the illustrated embodiment, meltblown fibers 36 are also extruded from an extrusion apparatus 45 on top of the continuous filaments 31 to form a laminated elastic strand layer 50.

To impart the desired elasticity to the composite, the elastic strand layer 50 is stretched in one or more directions. In FIG. 1, for example, the elastic strand layer 50 is stretched in the machine direction by passing through a first set of rolls 46 traveling at a speed that is slower than a second set of rolls 47. While four rolls are illustrated in FIG. 1, it should be understood that the number of rolls may be higher or lower, depending on the level of stretch that is desired and the degrees of stretching between each roll. To achieve the desired latent elasticity, various parameters of the stretching operation may be selectively controlled, including the stretch ratio, stretching temperature, and so forth. In some embodiments, for example, the elastic strand layer is stretched in the machine direction at a ratio of from about 2.0 to about 8.0, in some embodiments from about 3.0 to about 7.0, and in some embodiments, from about 3.5 to about 6.0. The stretch ratio may be determined by dividing the length of the stretched material by its length before stretching. The stretch ratio may also be approximately the same as the draw ratio, which may be determined by dividing the linear speed of the strand layer upon stretching (e.g., speed of the nip rolls) by the linear speed at which the strand layer is formed (e.g., speed of forming surface). In the illustrated embodiment, for example, the stretch ratio is determined by dividing the linear speed of the second set of rolls 47 by the linear speed of the forming surface 30.

The orientation temperature profile is also chosen to deliver the desired shrink mechanical properties, such as shrink tension and shrink percentage. More specifically, the orientation temperature is less than the melting temperature of the semi-crystalline polyolefin. For example, the elastic strand layer may be stretched at a temperature from about 15° C. to about 50° C., in some embodiments from about 25° C. to about 40° C., and in some embodiments, from about 30° C. to about 40° C. Preferably, the elastic strand layer is "cold drawn", i.e., stretched without the application of external heat (e.g., heated rolls), to improve latent elasticity.

A nonwoven web facing is also employed for laminating to the elastic strand layer 50. For example, a nonwoven web facing 33 may simply be unwound from a supply roll 22 as shown in FIG. 1. Alternatively, the nonwoven web facing 33 may be formed in-line, such as by dispensing polymer filaments from a pair of spinnerettes onto a conveyor assembly. The facing 33 may be compressed to form inter-filament bonding using a pair of nip rolls (not shown). Following compaction, the nonwoven web facing 33 is directed to a nip defined between rolls 58 for laminating to the elastic strand layer 50. In FIG. 1, a second nonwoven web facing 35 is also employed that originates from a supply roll 62.

As indicated above, the latent character of the elastic strand layer of the present invention may be enhanced by allowing it to relax prior to lamination to a nonwoven web facing. In some embodiments, for example, the elastic strand layer is allowed to relax about 10% or more, in some embodiments from about 15% to about 60%, and in some embodiments, from about 20% to about 50% in the machine direction. The aforementioned "relaxation percentage" may be determined by subtracting the relaxed length of the strand layer by the stretched length of the layer, dividing this difference by the stretched length; and then multiplying the quotient by 100. If desired, the stretched and relaxed lengths of the layers may be determined from the speed of rolls used during stretching and lamination. In the illustrated embodiment, for example, the relaxation percentage is determined by subtracting the linear speed of the nip rolls 58 from the linear speed of the rolls 47, dividing this difference by the linear speed of the rolls 47, and then multiplying the quotient by 100.

Various techniques may be utilized to bond the elastic strand layer 50 to the nonwoven web facings 33 and 35, including adhesive bonding; thermal bonding; ultrasonic bonding; microwave bonding; extrusion coating; and so forth. In one particular embodiment, one or both of the rolls 58 apply a pressure to the strand layer 50 and facings 33 and 35 to thermally bond the materials together. The rolls 58 may be smooth and/or contain a plurality of raised bonding elements. If desired, the elastic strand layer may itself act as an adhesive to facilitate bonding with the nonwoven web facings 33 and 35. Other adhesives may also be employed, such as Rextac 2730 and 2723 available from Huntsman Polymers of Houston, Tex., as well as adhesives available from Bostik Findley, Inc, of Wauwatosa, Wis. The type and basis weight of the adhesive used will be determined on the elastic attributes desired in the final composite and end use. For instance, the basis weight of the adhesive may be from about 1.0 to about 3.0 gsm. The adhesive may be applied to the nonwoven web facings and/or the elastic strand layer prior to lamination using any known technique, such as slot or melt spray adhesive systems.

The resulting composite 32 is wound and stored on a take-up roll 60. Optionally, the composite 32 may be allowed to slightly retract prior to winding on to the take-up roll 60. This may be achieved by using a slower linear velocity for the roll 60. More preferably, however, the composite 32 is kept under tension, such as by using the same linear velocity for the roll 60 as the speed of one or more of the nip rolls 58.

While not shown in FIG. 1, various additional potential processing and/or finishing steps known in the art, such as slitting, treating, printing graphics, etc., may be performed without departing from the spirit and scope of the invention. For instance, the composite may optionally be mechanically stretched in the cross-machine and/or machine directions to enhance extensibility. In one embodiment, the composite may be coursed through two or more rolls that have grooves in the CD and/or MD directions. Such grooved satellite/anvil roll arrangements are described in U.S. Patent Application Publication Nos. 2004/0110442 to Rhim, et al. and 2006/0151914 to Gerndt, et al., which are incorporated herein in their entirety by reference thereto for all purposes. For instance, the laminate may be coursed through two or more rolls that have grooves in the CD and/or MD directions. The grooved rolls may be constructed of steel or other hard material (such as a hard rubber). If desired, heat may be applied by any suitable method known in the art, such as heated air, infrared heaters, heated nipped rolls, or partial wrapping of the laminate around one or more heated rolls or steam canisters, etc. Heat may also be applied to the grooved rolls themselves. It should also be understood that other grooved roll arrangement are equally suitable, such as two grooved rolls positioned immediately adjacent to one another. Besides grooved rolls, other techniques may also be used to mechanically stretch the composite in one or more directions. For example, the composite may be passed through a tenter frame that stretches the composite. Such tenter frames are well known in the art and described, for instance, in U.S. Patent Application Publication No. 2004/0121687 to Morman, et al. The composite may also be necked. Suitable techniques necking techniques are described in U.S. Pat. Nos. 5,336,545, 5,226,992, 4,981,747 and 4,965,122 to Morman, as well as U.S. Patent Application Publication No. 2004/0121687 to Morman, et al., all of which are incorporated herein in their entirety by reference thereto for all purposes.

Figure 2:
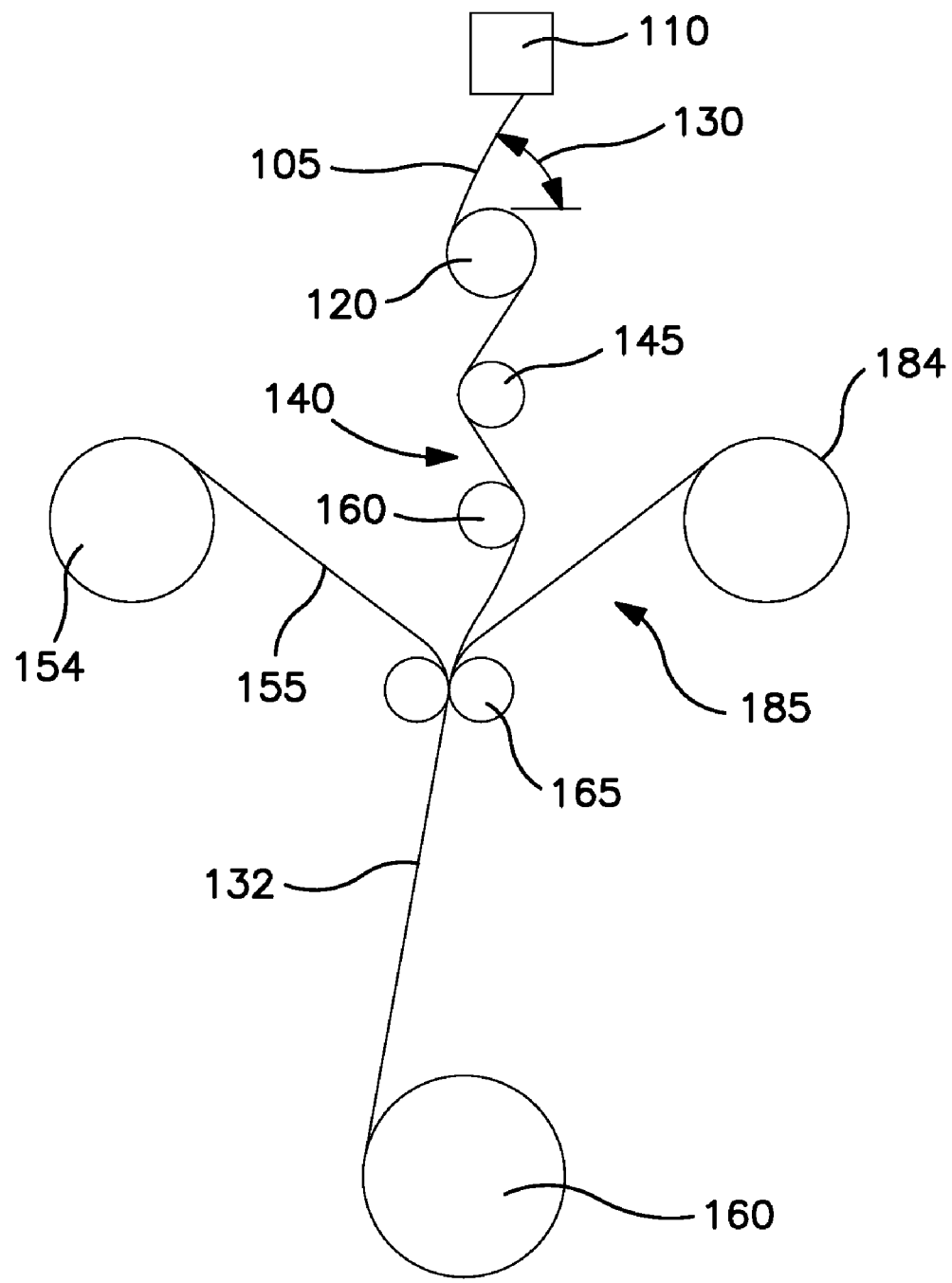
FIG. 2 schematically illustrates a method for forming a composite according to another embodiment of the present invention.

Although the embodiment shown in FIG. 1 depicts filaments formed in a "horizontal" extrusion process, it should be understood that other methods are equally contemplated by the present invention. In an alternative embodiment, for example, the filaments may be formed using a "vertical" extrusion process, such as described in U.S. Patent Application Publication No. 2002/0104608 to Welch, et al., which is incorporated herein in its entirety by reference thereto for all purposes. Referring to FIG. 2, for example, one embodiment of a method for forming a vertical filament laminate ("VFL") is shown. As depicted, the method employs a vertically arranged apparatus that includes an extruder 110 for extruding continuous molten filaments 105 downward from a die onto a chilled positioning roll 120. As the filaments travel over the surface of the roll 120, they are cooled and solidified. The chilled roll 120 may, for instance, have a temperature of about 40° F. to about 80° F. The die of the extruder 110 may be positioned with respect to the chilled roll 120 so that the continuous filaments meet the roll at a predetermined angle 130. An angled, or canted, orientation provides an opportunity for the filaments to emerge from the die at a right angle to the roll tangent point resulting in improved spinning, more efficient energy transfer, and generally longer die life. The angle 130 between the die exit of the extruder 110 and the vertical axis (or the horizontal axis of the first roll, depending on which angle is measured) may be as little as a few degrees or as much as 90°. The optimum angle may vary as a function of extrudate exit velocity, roll speed, vertical distance from the die to the roll, and horizontal distance from the die centerline to the top dead center of the roll.

After the filaments 105 are quenched and solidified, they are stretched or elongated using a series of stretch rolls 140. The series of stretch rolls 140 may include one or more individual stretch rolls, and suitably at least two stretch rolls 145 and 160 as shown in FIG. 2. The stretch rolls 145 and 160 rotate at a speed greater than a speed at which the chill roll 120 rotates, thereby stretching the filaments 105. In one embodiment of this invention, each successive roll rotates at a speed greater than the speed of the previous roll. Upon stretching, the filaments 105 are then allowed to relax prior to entering a nip formed between rolls 165. Nonwoven web facings 155 and 185 are unwound from supply rolls 154 and 184, respectively, and also supplied to the nip for lamination to the filaments 105. The resulting composite 132 is wound and stored on a take-up roll 160 as described above.

Generally speaking, composites may be formed according to the present invention that are relatively inelastic prior to heat activation. One parameter that is indicative of the dimensional stability of the composite prior to heat activation is the percent strain that it undergoes at a load of 2000 grams-force per 3 inches wide (sample width) according to the "stretch to stop" test, which is described in more detail below. More specifically, the composite typically has a percent strain of about 50% or less in the machine direction, in some embodiments about 40% or less in the machine direction, and in some embodiments, about 25% or less in the machine direction prior to heat activation. After heat shrinkage, the composite typically has a percent strain of about 50% or more in the machine direction, in some embodiments about 75% or more in the machine direction, and in some embodiments, from about 100% to about 200% in the machine direction. Furthermore, the potential shrinkage of the composite may be about 40% or more, in some embodiments about 50% or more, and in some embodiments, about 60% or more.

As a result of the present invention, the composite may be more easily processed into an end product because it is less elastic prior to activation, and thus more dimensionally stable. This allows the composite to be more readily processed, e.g., printed, rolled or unrolled, converted into a final product, etc. In one embodiment, for example, a latent elastic composite may be incorporated into an absorbent article. During the conversion process, the latent elastic composite may be activated through the application of heat, such as during the curing process for an adhesive used to attach together various components of the product. Because the latent elastic composite has a greater dimensional stability prior to activation than highly elastic materials, enhanced processing efficiencies may be realized. For example, the composite need not be maintained in a mechanically stretched condition during attachment to other components of the product. This allows for greater freedom in the location and manner in which the adhesive is applied.

The latent elastic composite of the present invention may be used in a wide variety of applications. As noted above, for example, the elastic composite may be used in an absorbent article. An "absorbent article" generally refers to any article capable of absorbing water or other fluids. Examples of some absorbent articles include, but are not limited to, personal care absorbent articles, such as diapers, training pants, absorbent underpants, incontinence articles, feminine hygiene products (e.g., sanitary napkins), swim wear, baby wipes, and so forth; medical absorbent articles, such as garments, fenestration materials, underpads, bedpads, bandages, absorbent drapes, and medical wipes; food service wipers; clothing articles; and so forth. Materials and processes suitable for forming such absorbent articles are well known to those skilled in the art. Typically, absorbent articles include a substantially liquid-impermeable layer (e.g., outer cover), a liquid-permeable layer (e.g., bodyside liner, surge layer, etc.), and an absorbent core. In one particular embodiment, the elastic strand layer of the present invention may be used in providing elastic waist, leg cuff/gasketing, stretchable ear, side panel or stretchable outer cover applications.

Figure 3:
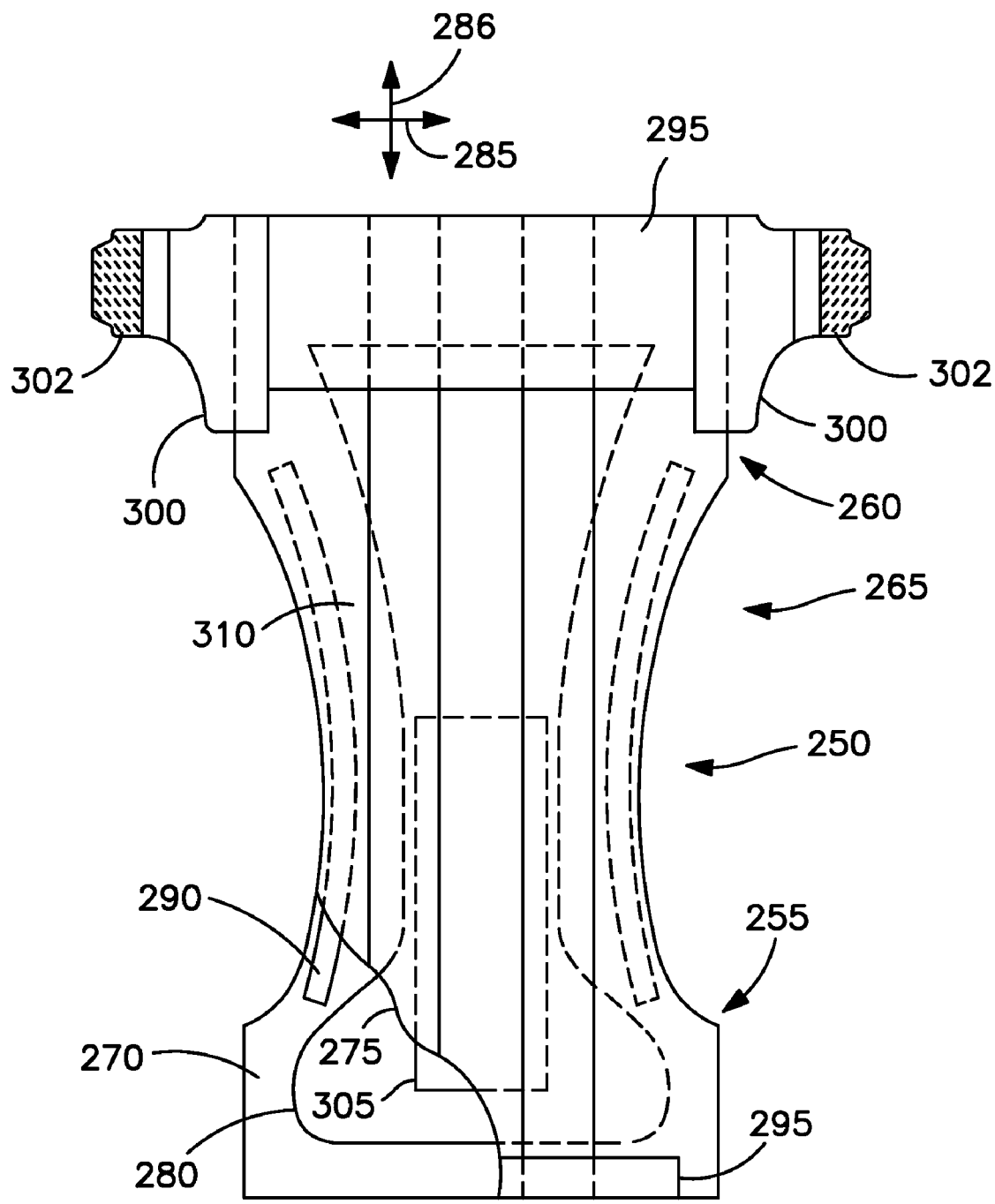
FIG. 3 is a perspective view of a personal care product that may be formed in accordance with one embodiment of the present invention.

Various embodiments of an absorbent article that may be formed according to the present invention will now be described in more detail. Referring to FIG. 3, for example, one embodiment of a disposable diaper 250 is shown that generally defines a front waist section 255, a rear waist section 260, and an intermediate section 265 that interconnects the front and rear waist sections. The front and rear waist sections 255 and 260 include the general portions of the diaper which are constructed to extend substantially over the wearer's front and rear abdominal regions, respectively, during use. The intermediate section 265 of the diaper includes the general portion of the diaper that is constructed to extend through the wearer's crotch region between the legs. Thus, the intermediate section 265 is an area where repeated liquid surges typically occur in the diaper.

The diaper 250 includes, without limitation, an outer cover, or backsheet 270, a liquid permeable bodyside liner, or topsheet, 275 positioned in facing relation with the backsheet 270, and an absorbent core body, or liquid retention structure, 280, such as an absorbent pad, which is located between the backsheet 270 and the topsheet 275. The backsheet 270 defines a length, or longitudinal direction 286, and a width, or lateral direction 285 which, in the illustrated embodiment, coincide with the length and width of the diaper 250. The liquid retention structure 280 generally has a length and width that are less than the length and width of the backsheet 270, respectively. Thus, marginal portions of the diaper 250, such as marginal sections of the backsheet 270 may extend past the terminal edges of the liquid retention structure 280. In the illustrated embodiments, for example, the backsheet 270 extends outwardly beyond the terminal marginal edges of the liquid retention structure 280 to form side margins and end margins of the diaper 250. The topsheet 275 is generally coextensive with the backsheet 270 but may optionally cover an area that is larger or smaller than the area of the backsheet 270, as desired.

To provide improved fit and to help reduce leakage of body exudates from the diaper 250, the diaper side margins and end margins may be elasticized with suitable elastic members, as further explained below. For example, as representatively illustrated in FIG. 3, the diaper 250 may include leg elastics 290 constructed to operably tension the side margins of the diaper 250 to provide elasticized leg bands which can closely fit around the legs of the wearer to reduce leakage and provide improved comfort and appearance. Waist elastics 295 are employed to elasticize the end margins of the diaper 250 to provide elasticized waistbands. The waist elastics 295 are configured to provide a resilient, comfortably close fit around the waist of the wearer. The latently elastic materials of the present invention are suitable for use as the leg elastics 290 and waist elastics 295. Exemplary of such materials are laminate sheets that either comprise or are adhered to the backsheet, such that elastic constrictive forces are imparted to the backsheet 270.

As is known, fastening means, such as hook and loop fasteners, may be employed to secure the diaper 250 on a wearer. Alternatively, other fastening means, such as buttons, pins, snaps, adhesive tape fasteners, cohesives, fabric-and-loop fasteners, or the like, may be employed. In the illustrated embodiment, the diaper 250 includes a pair of side panels 300 (or ears) to which the fasteners 302, indicated as the hook portion of a hook and loop fastener, are attached. Generally, the side panels 300 are attached to the side edges of the diaper in one of the waist sections 255, 260 and extend laterally outward therefrom. The side panels 300 may be elasticized or otherwise rendered elastomeric by use of a latently elastic materials of the present invention. Examples of absorbent articles that include elasticized side panels and selectively configured fastener tabs are described in PCT Patent Application WO 95/16425 to Roessler; U.S. Pat. No. 5,399,219 to Roessler et al.; U.S. Pat. No. 5,540,796 to Fries; and U.S. Pat. No. 5,595,618 to Fries, each of which is incorporated herein in its entirety by reference thereto for all purposes.

The diaper 250 may also include a surge management layer 305, located between the topsheet 275 and the liquid retention structure 280, to rapidly accept fluid exudates and distribute the fluid exudates to the liquid retention structure 280 within the diaper 250. The diaper 250 may further include a ventilation layer (not illustrated), also called a spacer, or spacer layer, located between the liquid retention structure 280 and the backsheet 270 to insulate the backsheet 270 from the liquid retention structure 280 to reduce the dampness of the garment at the exterior surface of a breathable outer cover, or backsheet, 270. Examples of suitable surge management layers 305 are described in U.S. Pat. No. 5,486,166 to Bishop and U.S. Pat. No. 5,490,846 to Ellis.

As representatively illustrated in FIG. 3, the disposable diaper 250 may also include a pair of containment flaps 310 which are configured to provide a barrier to the lateral flow of body exudates. The containment flaps 310 may be located along the laterally opposed side edges of the diaper adjacent the side edges of the liquid retention structure 280. Each containment flap 310 typically defines an unattached edge that is configured to maintain an upright, perpendicular configuration in at least the intermediate section 265 of the diaper 250 to form a seal against the wearer's body. The containment flaps 310 may extend longitudinally along the entire length of the liquid retention structure 280 or may only extend partially along the length of the liquid retention structure. When the containment flaps 310 are shorter in length than the liquid retention structure 280, the containment flaps 310 can be selectively positioned anywhere along the side edges of the diaper 250 in the intermediate section 265. Such containment flaps 310 are generally well known to those skilled in the art. For example, suitable constructions and arrangements for containment flaps 310 are described in U.S. Pat. No. 4,704,116 to Enloe.

The diaper 250 may be of various suitable shapes. For example, the diaper may have an overall rectangular shape, T-shape or an approximately hour-glass shape. In the shown embodiment, the diaper 250 has a generally I-shape. Other suitable components which may be incorporated on absorbent articles of the present invention may include waist flaps and the like which are generally known to those skilled in the art. Examples of diaper configurations suitable for use in connection with the latently elastic materials of the present invention that may include other components suitable for use on diapers are described in U.S. Pat. No. 4,798,603 to Meyer et al.; U.S. Pat. No. 5,176,668 to Bernardin; U.S. Pat. No. 5,176,672 to Bruemmer et al.; U.S. Pat. No. 5,192,606 to Proxmire et al.; and U.S. Pat. No. 5,509,915 to Hanson et al., which are incorporated herein in their entirety by reference thereto for all purposes.

The various regions and/or components of the diaper 201 may be assembled together using any known attachment mechanism, such as adhesive, ultrasonic, thermal bonds, etc. Suitable adhesives may include, for instance, hot melt adhesives, pressure-sensitive adhesives, and so forth. When utilized, the adhesive may be applied as a uniform layer, a patterned layer, a sprayed pattern, or any of separate lines, swirls or dots. In the illustrated embodiment, for example, the topsheet 275 and backsheet 270 may be assembled to each other and to the liquid retention structure 280 with lines of adhesive, such as a hot melt, pressure-sensitive adhesive. Similarly, other diaper components, such as the elastic members 290 and 295, fastening members 302, and surge layer 305 may be assembled into the article by employing the above-identified attachment mechanisms.

Although various configurations of a diaper have been described above, it should be understood that other diaper and absorbent article configurations are also included within the scope of the present invention. In addition, the present invention is by no means limited to diapers. In fact, several examples of absorbent articles are described in U.S. Pat. No. 5,649,916 to DiPalma, et al.; U.S. Pat. No. 6,110,158 to Kielpikowski; U.S. Pat. No. 6,663,611 to Blaney, et al., which are incorporated herein in their entirety by reference thereto for all purposes. Further, other examples of personal care products that may incorporate such materials are training pants (such as in side panel materials) and feminine care products. By way of illustration only, training pants suitable for use with the present invention and various materials and methods for constructing the training pants are disclosed in U.S. Pat. No. 6,761,711 to Fletcher et al.; U.S. Pat. No. 4,940,464 to Van Gompel et al.; U.S. Pat. No. 5,766,389 to Brandon et al.; and U.S. Pat. No. 6,645,190 to Olson et al., which are incorporated herein in their entirety by reference thereto for all purposes.

The present invention may be better understood with reference to the following examples.

Test Methods

% Heat Shrinkage

To measure heat-activated retraction, marks spaced 100 millimeters apart are placed on the material while it is still under tension on the roll. The material is then released from tension on the roll and a length of material containing the marks is cut from the roll. Immediately after releasing the material and cutting it, the distance between the marks is measured again to determine the initial length (Before Heated Retraction Length or "BHRL"). The material is then submerged in water (160° F.) for at least 30 seconds, but no more than 1 minute. Thereafter, the distance between the marks is again measured (After Heated Retraction Length or "AHRL"). The percent shrinkage is indicative of the latent elasticity of the material and is calculated by the following equation:

$$\% \text{ shrinkage} = 100 * (BHRL - AHRL)/BHRL$$

Three measurements are averaged for each sample to be tested. The measurements are taken at ambient conditions.

Cycle Testing

The materials were tested using a cyclical testing procedure to determine load loss and percent set. In particular, 2-cycle testing was utilized to 100% defined elongation. For this test, the sample size was 3 inches (7.6 centimeters) in the cross-machine direction by 6 inches in the machine direction. The Grip size was 3 inches (7.6 centimeters) in width. The grip separation was 4 inches. The samples were loaded such that the machine direction of the sample was in the vertical direction. A preload of approximately 20 to 30 grams was set. The test pulled the sample to 100% elongation at a speed of 20 inches (50.8 centimeters) per minute, and then immediately (without pause) returned to the zero at a speed of 20 inches (50.8 centimeters) per minute. The results of the test data are all from the first and second cycles. The testing was done on a Sintech Corp. constant rate of extension tester 2/S with a Renew MTS mongoose box (control) using TESTWORKS 4.07b software (Sintech Corp, of Cary, N.C.). The tests were conducted under ambient conditions.

Stretch-to-Stop

The materials were tested to determine the ability of the material to undergo elongation upon application of a tensioning. More specifically, the percent strain of the material at a load of 2000 grams-force was determined by subtracting the maximum extended dimension of the material from its unextended dimension, dividing that difference by the unextended dimension, and then multiplying by 100. Such measurements are determined using the "strip elongation test", which is substantially in accordance with the specifications of ASTM D5035-95. The test uses two clamps, each having two jaws with each jaw having a facing in contact with the sample. The clamps hold the material in the same plane and move apart at a specified rate of extension. A sample size of 3 inches (7.6 centimeters) in the cross-machine direction by 7 inches (17.8 centimeters) in the machine direction was selected. The grip size was 3 inches (7.6 centimeters) in width, and intermeshing grips were utilized so that material would not slip while tested. The grip separation was 100 millimeters. The samples were loaded so that the machine direction of the sample was in the vertical direction. A preload of approximately 20 to 30 grams-force was set. The test pulled the sample until 2000 grams-force of tension was produced, and then the test stopped. The test speed was 500 millimeters per minute of extension or strain. The test reported the elongation or strain in percent from start when 2000 grams-force of tension was produced (per 3 inches in width of the material). The testing was done on a Sintech Corp. constant rate of extension tester 2/S with a Renew MTS mongoose box (controller) using TESTWORKS 4.07b software (Sintech Corp, of Cary, N.C.). The tests were conducted under ambient conditions. Results are generally reported as an average of three specimens and may be performed with the specimen in the cross direction (CD) and/or the machine direction (MD).

EXAMPLE 1

Six samples (Nos. 1-6) of a continuous filament/meltblown laminate were initially formed using the "horizontal" method shown in FIG. 1. The filaments were formed from 100 wt. % KRATON® MD6673 (Kraton Polymers, LLC of Houston Tex.). KRATON® MD6673 contains 68 wt. % of a styrene-ethylene-butylene-styrene block copolymer (KRATON® MD6937), 20 wt. % REGALREZ™ 1126 (Eastman Chemical) and 12 wt. % EPOLENE™ C-10 polyethylene wax (Eastman Chemical). The meltblown web was formed from 80 wt. % of AFFINITY EG8185 (Dow Chemical Co.) and 20 wt. % REGALREZ™ 1126 (Eastman Chemical). AFFINITY EG8185 is a metallocene-catalyzed polyethylene plastomer having a density of 0.885 grams per cubic centimeter, a peak melting temperature of 83° C., and a melt index of 30 grams per 10 minutes (190° C., 2.16 kg).

A 1.5" Killion extruder was used to extrude the parallel continuous filaments and a 3" Beloit extruder was used to produce the meltblown fibers. The extruder temperatures were set at 500° F. and 420° F. for the 1.5" and 3" extruders, respectively. The filament die had 12 holes per inch, each hole having a diameter of 0.9 millimeters. The filaments were first laid down on a foraminous wire and then the meltblown fibers were formed on top of the filaments. The filament/meltblown structure was removed from the forming wire at a speed of 20 feet per minute and then passed through S-wrap rollers operating at a speed of 100 feet per minute, thereby stretching the structure at a stretch ratio of about 5.0 in the machine direction. The samples were then passed through two smooth calender rolls and thermally bonded to a polypropylene spunbond facing having a basis weight of approximately 13.6 grams per square meter. For Sample Nos. 1-3, the calender rolls operated at a speed of 70 feet per minute so that the filament/meltblown structure was allowed to relax about 30% before lamination to the spunbond facing. For Sample Nos. 4-6, the calender rolls operated at a speed of 60 feet per minute so that the filament/meltblown structure was allowed to relax about 40% before lamination to the spunbond facing. The resulting laminates were then wound onto a roll operating at the same speed as the smooth roll calender rolls.

The specific processing conditions and web properties are set forth in more detail below in Tables 1-2.

TABLE 1

Process Conditions

| Sample | Filament Extruder Speed (RPM) | Meltblown Extruder Speed (RPM) | Wire Speed (ft/min) | S-Wrap #1 Speed (ft/min) | Stretch Ratio | S-wrap #2 Speed (ft/min) | Relaxation % | Calender Speed (ft/min) | Winder Speed (ft/min) |
|---|---|---|---|---|---|---|---|---|---|
| 1 | 8.6 | 9.0 | 20 | 20 | 5 | 100 | 30 | 70 | 70 |
| 2 | 6.9 | 9.0 | 20 | 20 | 5 | 100 | 30 | 70 | 70 |
| 3 | 5.2 | 9.0 | 20 | 20 | 5 | 100 | 30 | 70 | 70 |
| 4 | 5.2 | 9.0 | 20 | 20 | 5 | 100 | 40 | 60 | 60 |
| 5 | 6.9 | 9.0 | 20 | 20 | 5 | 100 | 40 | 60 | 60 |
| 6 | 8.6 | 9.0 | 20 | 20 | 5 | 100 | 40 | 60 | 60 |

TABLE 2

Web Properties

| Sample | Filament Basis Wt. After Stretching (gsm) | Meltblown Basis Wt. After Stretching (gsm) | Ratio of Filament Basis Wt. to Meltblown Basis Wt. |
|---|---|---|---|
| 1 | 25 | 10 | 2.45 |
| 2 | 20 | 10 | 2.03 |
| 3 | 15 | 10 | 1.50 |
| 4 | 15 | 10 | 1.50 |
| 5 | 20 | 10 | 3.03 |
| 6 | 25 | 10 | 2.45 |

EXAMPLE 2

Three (3) samples (Sample Nos. 7-9) of a continuous filament/meltblown laminate were initially formed using the "horizontal" method shown in FIG. 1. The filaments were formed from 100 wt. % KRATON® MD6673 (Kraton Polymers, LLC of Houston Tex.). The meltblown web was formed from 80 wt. % of AFFINITY EG8185 (Dow Chemical Co.) and 20 wt. % REGALREZ™ 1126 (Eastman Chemical). A 1.5" Killion extruder was used to extrude the parallel continuous filaments and a 3" Beloit extruder was used to produce the meltblown fibers. The extruder temperatures were set at 500° F. and 420° F. for the 1.5" and 3" extruders, respectively. The filament die had 12 holes per inch, each hole having a diameter of 0.9 millimeters. The filaments were first laid down on a foraminous wire and then the meltblown fibers were formed on top of the filaments. The filament/meltblown structure was removed from the forming wire at a speed of 20 feet per minute and then passed through S-wrap rollers operating at a speed of 100 feet per minute, thereby stretching the structure at a stretch ratio of about 5.0 in the machine direction. The samples were then passed through two smooth calender rolls and thermally bonded to a polypropylene spunbond facing having a basis weight of approximately 13.6 grams per square meter. The calender rolls operated at a speed of 100 feet per minute so that the filament/meltblown structure remained under tension during lamination. The resulting laminates were then wound onto a roll operating at a speed of 70 feet per minute.

The specific processing conditions and web properties are set forth in more detail below in Tables 3-4.

TABLE 3

| | Process Conditions | | | | | | |
|---|---|---|---|---|---|---|---|
| Sample | Filament Extruder Speed (RPM) | Meltblown Extruder Speed (RPM) | Wire Speed (ft/min) | S-Wrap #1 Speed (ft/min) | Strech Ratio | Calender Speed (ft/min) | Winder Speed (ft/min) |
| 7 | 8.6 | 9.0 | 20 | 20 | 5 | 100 | 70 |
| 8 | 6.9 | 9.0 | 20 | 20 | 5 | 100 | 70 |
| 9 | 5.2 | 9.0 | 20 | 20 | 5 | 100 | 70 |

TABLE 4

| | Web Properties | | |
|---|---|---|---|
| Sample | Filament Basis Wt. After Stretching (gsm) | Meltblown Basis Wt. After Streching (gsm) | Ratio of Filament Basis Wt. to Meltblown Basis Wt. |
| 7 | 25 | 10 | 2.45 |
| 8 | 20 | 10 | 2.03 |
| 9 | 15 | 10 | 1.50 |

EXAMPLE 3

The materials of Examples 1 and 2 were heat activated and cycle tested as described above. The results are set forth below in Table 5.

TABLE 5

| | | | | Composite Properties | | | | | | | |
|---|---|---|---|---|---|---|---|---|---|---|---|
| | | | | Cycle 1 | | | | Cycle 2 | | | |
| Sample | BHRL (mm) | AHRL (mm) | % Shrinkage | Load up 50% | Load up 100% | Load down 50% | Hyst. % | Load up 50% | Load up 100% | Load down 50% | Set % |
| 1 | 87 | 45 | 48 | 917 | 1239 | 608 | 30.1 | 751 | 1201 | 591 | 9.0 |
| 2 | 83 | 39 | 53 | 770 | 1065 | 508 | 29.9 | 629 | 1031 | 494 | 9.4 |
| 3 | 90 | 36 | 60 | 569 | 841 | 343 | 33.6 | 452 | 813 | 333 | 12.1 |
| 4 | 95 | 42 | 56 | 583 | 913 | 337 | 35.9 | 454 | 877 | 325 | 12.1 |
| 5 | 91 | 43 | 53 | 743 | 1060 | 462 | 33.4 | 591 | 1028 | 448 | 10.3 |
| 6 | 90 | 46 | 49 | 900 | 1253 | 583 | 31.5 | 729 | 1213 | 568 | 9.4 |
| 7 | 91 | 52 | 43 | 879 | 1182 | 589 | 29.5 | 727 | 1150 | 574 | 9.0 |
| 8 | 87 | 45 | 48 | 728 | 992 | 475 | 30.8 | 599 | 965 | 462 | 10.1 |
| 9 | 84 | 41 | 52 | 633 | 880 | 384 | 35.1 | 506 | 856 | 374 | 10.9 |

As indicated, the samples provided good elastic behavior after heat activation as exhibited by their hysteresis and set as obtained through cycle testing. Additionally, the samples exhibited good latency behavior through their BHRL and AHRL results. Additional portions of Sample Nos. 2 and 8 were further heat activated and "stretch to stop" tested as described above. The results are set forth below in Table 6.

TABLE 6

Composite Properties

| Sample | BHRL (mm) | AHRL (mm) | % Shrinkage | % Stretch to Stop (Before Heat Shrinkage) | % Stretch to Stop (After Heat Shrinkage) |
|---|---|---|---|---|---|
| 2 | 93 | 44 | 53 | 22 | 159 |
| 8 | 90 | 45 | 50 | 71 | 241 |

As indicated, Sample No. 2 had a low stretch-to-stop value prior to heat activation and high value after heat activation, which is indicative of a material that is relatively inelastic prior to heat activation, but elastic after heat activation.

While the invention has been described in detail with respect to the specific embodiments thereof, it will be appreciated that those skilled in the art, upon attaining an understanding of the foregoing, may readily conceive of alterations to, variations of, and equivalents to these embodiments. Accordingly, the scope of the present invention should be assessed as that of the appended claims and any equivalents thereto.

What is claimed is:

1. A method of forming a nonwoven composite having latent elasticity, the method comprising:
    forming an elastic strand layer comprising a plurality of strands in the form of filaments laminated to a meltblown web, wherein the meltblown web contains a single-site catalyzed semi-crystalline polyolefin and the filaments contain a thermoplastic elastomer, the single-site catalyzed semi-crystalline polyolefin having a density of from about 0.85 to about 0.87 grams per cubic centimeter and comprising at least 70 weight percent of the polymer content of the meltblown web;
    stretching the elastic strand layer in the machine direction at a stretch ratio from about 2.0 to about 8.0, thereby forming a stretched elastic strand layer;
    allowing the stretched elastic strand layer to relax to achieve a relaxation percentage of about 10% or more; and
    laminating a nonwoven web facing to the relaxed elastic strand layer to form a generally inelastic composite that exhibits a percent strain of about 50% or less when subjected to a load in the machine direction of 2000 grams-force per 3 inches wide, wherein the composite is capable of being heat activated to form an elastic composite.

2. The method of claim 1, wherein the elastic strand layer is stretched at a stretch ratio of from about 3.5 to about 6.0.

3. The method of claim 1, wherein the relaxation percentage is about 20% to about 50%.

4. The method of claim 1, wherein the elastic strand layer is also stretched in the cross-machine direction.

5. The method of claim 1, further comprising winding the composite onto a roll, wherein the composite is substantially inhibited from retracting in the machine direction during winding onto the roll.

6. The method of claim 1, wherein the thermoplastic elastomer is selected from the group consisting of styrene-butadiene, styrene-isoprene, styrene-butadiene-styrene, styrene-isoprene-styrene, styrene-(ethylene-butylene), styrene-(ethylene-propylene), styrene-(ethylene-butylene)-styrene, styrene-(ethylene-propylene)-styrene, styrene-(ethylene-butylene)-styrene-(ethylene-butylene), styrene-(ethylene-propylene)-styrene-(ethylene-propylene), and styrene-ethylene-(ethylene-propylene)-styrene, and combinations thereof.

7. The method of claim 1, wherein the semi-crystalline polyolefin is an ethylene/α-olefin copolymer, propylene/α-olefin copolymer, or a combination thereof.

8. The method of claim 1, wherein thermoplastic elastomers constitute from about 40 wt. % to about 95 wt. % of the elastic strand layer and semi-crystalline polyolefins constitute from about 5 wt. % to about 60 wt. % of the elastic strand layer.

9. The method of claim 1, wherein thermoplastic elastomers constitute from about 45 wt. % to about 90 wt. % of the elastic strand layer and semi-crystalline polyolefins constitute from about 15 wt. % to about 55 wt. % of the elastic strand layer.

10. The method of claim 1, wherein the strands are in the form of an array of continuous filaments.

11. The method of claim 10, wherein the filaments are formed from a blend of the thermoplastic elastomer and semi-crystalline polyolefin.

12. The method of claim 1, wherein the ratio of the basis weight of the filaments to the basis weight of the meltblown web is from about 1.2 to about 5.0.

13. The method of claim 1, wherein the nonwoven web facing contains a spunbond web, meltblown web, or a combination thereof.

14. The method of claim 1, further comprising laminating a second nonwoven web facing to the relaxed elastic strand layer.

15. The method of claim 1, wherein the elastic strand layer exhibits a heat shrinkage of about 40% or more after being heated in water at 160° F. for 30 seconds to 1 minute.

16. The method of claim 1, wherein the elastic strand layer exhibits a heat shrinkage of about 50% or more after being heated in water at 160° F. for 30 seconds to 1 minute.

17. The method of claim 1, wherein the composite exhibits a percent strain of about 40% or less when subjected to a load of 2000 grams-force per 3 inches wide in the machine direction prior to heat activation.

18. The method of claim 1, wherein the composite exhibits a percent strain of about 25% or less when subjected to a load in the machine direction of 2000 grams-force per 3 inches wide prior to heat activation.

19. The method of claim 1, wherein after heat activation, the composite exhibits a percent strain of about 75% or more when subjected to a load of 2000 grams-force per 3 inches wide in the machine direction.

20. The method of claim 1, wherein after heat activation, the composite exhibits a percent strain of from about 100% to about 200% when subjected to a load in the machine direction of 2000 grams-force per 3 inches wide.

21. The method of claim 1, wherein the thermoplastic elastomer comprises at least 70 weight percent of the filaments.

22. A method for forming an absorbent article, the method comprising:

fastening a nonwoven composite to one or more components of the article, the nonwoven composite comprising an elastic strand layer laminated to a nonwoven web facing, the elastic strand layer comprising a plurality of elastic strands in the form of filaments laminated to a meltblown web, the elastic strand layer being formed from at least one thermoplastic elastomer and at least one single-site catalyzed semi-crystalline polyolefin, wherein the meltblown web contains the at least one single-site catalyzed semi-crystalline polyolefin and the filaments contain the thermoplastic elastomer, the at least one single-site catalyzed semi-crystalline polyolefin having a density of from about 0.85 to about 0.87 grams per cubic centimeter and comprising at least 70 weight percent of the meltblown web, wherein the semi-crystalline polyolefin constitutes from about 40 wt. % to about 95 wt. % of the elastic strand layer and the thermoplastic elastomer constitutes from about 5 wt. % to about 60 wt. % of the elastic strand layer, wherein the composite is generally inelastic and exhibits a percent strain of about 50% or less when subjected to a load in the machine direction of 2000 grams-force per 3 inches wide;

heating the nonwoven composite; and allowing the nonwoven to retract, thereby increasing the stretchability of the composite.

23. The method of claim 22, wherein the thermoplastic elastomer is selected from the group consisting of styrene-butadiene, styrene-isoprene, styrene-butadiene-styrene, styrene-isoprene-styrene, styrene-(ethylene-butylene), styrene-(ethylene-propylene), styrene-(ethylene-butylene)-styrene, styrene-(ethylene-propylene)-styrene, styrene-(ethylene-butylene)-styrene-(ethylene-butylene), styrene-(ethylene-propylene)-styrene-(ethylene-propylene), and styrene-ethylene-(ethylene-propylene)-styrene, and combinations thereof.

24. The method of claim 22, wherein the semi-crystalline polyolefin is an ethylene/α-olefin copolymer, propylene/a-olefin copolymer, or a combination thereof.

25. The method of claim 22, wherein the thermoplastic elastomer constitutes from about 45 wt. % to about 90 wt. % of the elastic strand layer and the semi-crystalline polyolefin constitutes from about 10 wt. % to about 55 wt. % of the elastic strand layer.

26. The method of claim 22, wherein the strands are in the form of an array of continuous filaments.

27. The method of claim 22, wherein an adhesive is used to fasten The composite.

28. The method of claim 22, wherein the composite is heated at a temperature of from about 50° C. to about 100° C.

29. The method of claim 22, wherein the composite is heated at a temperature of from about 70° C. to about 80° C.

30. The method of claim 22, wherein prior to heating, the composite exhibits a percent strain of about 40% or less when subjected to a load of 2000 grams-force per 3 inches wide in the machine direction.

31. The method of claim 22, wherein the thermoplastic elastomer comprises at least 70 weight percent of the filaments.

* * * * *